US012599181B2

(12) United States Patent
Griffiths et al.

(10) Patent No.: US 12,599,181 B2
(45) Date of Patent: Apr. 14, 2026

(54) MOISTURE LOCK FLUID RETENTION ASSEMBLIES, GARMENTS INCLUDING THE SAME, AND RELATED METHODS

(71) Applicant: Knix Wear Inc., Toronto (CA)

(72) Inventors: Joanna Griffiths, Toronto (CA); Julie Power, Toronto (CA); Linda Kritikos, Toronto (CA); Aditi Shankar, Toronto (CA)

(73) Assignee: Knix Wear Inc., Toronto (CA)

( * ) Notice: Subject to any disclaimer, the term of this patent is extended or adjusted under 35 U.S.C. 154(b) by 95 days.

(21) Appl. No.: 18/419,152

(22) Filed: Jan. 22, 2024

(65) Prior Publication Data

US 2025/0234939 A1     Jul. 24, 2025

(51) Int. Cl.
| | |
|---|---|
| *A41B 9/12* | (2006.01) |
| *A61F 13/15* | (2006.01) |
| *A61F 13/49* | (2006.01) |

(52) U.S. Cl.
CPC .......... *A41B 9/12* (2013.01); *A61F 13/15203* (2013.01); *A61F 13/15268* (2013.01);
(Continued)

(58) Field of Classification Search
CPC ...... A61F 13/15268; A61F 2013/15276; A61F 13/4755; A61F 13/505; A61F 13/51;
(Continued)

(56) References Cited

U.S. PATENT DOCUMENTS

| | | | |
|---|---|---|---|
| 2,985,170 | A | 5/1961 | Title |
| 3,489,149 | A | 1/1970 | Larson |

(Continued)

FOREIGN PATENT DOCUMENTS

| | | |
|---|---|---|
| AU | 2006209375 A1 | 10/2006 |
| AU | 2014218471 B2 | 10/2016 |

(Continued)

OTHER PUBLICATIONS

Swantko, Kathlyn, "Forming A New Bond," FabricTrends: A GearTrends Supplement, 2004, pp. 12-14.

(Continued)

*Primary Examiner* — Michele Kidwell
(74) *Attorney, Agent, or Firm* — Kolitch Romano Dascenzo Gates LLP

(57) ABSTRACT

Garments may include a fluid retention assembly coupled to the garment base interior side and having an outer perimeter. The fluid retention assembly includes an absorbent layer configured to absorb fluid excreted from the wearer when the garment is worn, and a moisture-impermeable layer that underlies the absorbent layer and separates the garment base interior side from the absorbent-layer exterior side. The moisture-impermeable layer is configured to restrict fluid from exiting the fluid retention assembly to the garment base interior side. The moisture-impermeable layer extends to and wraps around at least a portion of the outer perimeter of the fluid retention assembly and is coupled to the assembly interior side, thereby creating a moisture lock to retain fluids within the fluid retention assembly.

24 Claims, 11 Drawing Sheets

(52) U.S. Cl.
CPC .... *A61F 13/49006* (2013.01); *A41B 2400/62* (2013.01); *A61F 2013/15016* (2013.01)

(58) Field of Classification Search
CPC .............. A61F 13/514; A61F 13/15203; A61F 13/49006; A61F 13/496; A61F 2013/15016; A41B 2400/62; A41B 9/12
See application file for complete search history.

(56) References Cited

U.S. PATENT DOCUMENTS

| | | | |
|---|---|---|---|
| 3,608,551 | A | 9/1971 | Seijo |
| 3,687,141 | A | 8/1972 | Matsuda |
| 4,044,769 | A | 8/1977 | Papajohn |
| 4,205,679 | A | 6/1980 | Repke et al. |
| 4,352,356 | A | 10/1982 | Tong |
| 4,355,425 | A | 10/1982 | Jones et al. |
| 4,560,381 | A | 12/1985 | Southwell |
| 4,695,279 | A * | 9/1987 | Steer ..................... A61F 13/472 |
| | | | 604/397 |
| 4,781,962 | A | 11/1988 | Zamarripa et al. |
| 4,813,950 | A | 3/1989 | Branch |
| 4,847,134 | A | 7/1989 | Fahrenkrug et al. |
| 4,898,594 | A * | 2/1990 | Cottenden ............. A61F 13/491 |
| | | | 604/397 |
| 4,940,464 | A * | 7/1990 | Van Gompel ..... A61F 13/15593 |
| | | | 604/385.22 |
| 5,151,092 | A | 9/1992 | Buell et al. |
| 5,167,897 | A | 12/1992 | Weber et al. |
| 5,217,782 | A | 6/1993 | Moretz et al. |
| 5,224,941 | A | 7/1993 | Simmons |
| 5,308,346 | A | 5/1994 | Sneller et al. |
| 5,342,338 | A | 8/1994 | Roe |
| 5,360,420 | A | 11/1994 | Cook et al. |
| 5,368,910 | A | 11/1994 | Langdon |
| 5,411,498 | A | 5/1995 | Fahrenkrug et al. |
| 5,449,352 | A | 9/1995 | Nishino et al. |
| 5,500,270 | A | 3/1996 | Langdon et al. |
| 5,507,895 | A | 4/1996 | Suekane |
| 5,518,801 | A | 5/1996 | Chappell et al. |
| 5,665,452 | A | 9/1997 | Langdon et al. |
| 5,677,028 | A | 10/1997 | Ravella |
| 5,693,169 | A | 12/1997 | Langdon et al. |
| H1732 | H | 6/1998 | Johnson |
| H1746 | H | 8/1998 | Carrier et al. |
| 5,851,204 | A | 12/1998 | Mizutani |
| 5,855,573 | A | 1/1999 | Johansson |
| 5,879,487 | A | 3/1999 | Ravella |
| 5,899,895 | A | 5/1999 | Robles et al. |
| 5,921,974 | A | 7/1999 | Kikuchi |
| 6,117,523 | A | 9/2000 | Sugahara |
| 6,120,487 | A | 9/2000 | Ashton |
| 6,149,497 | A | 11/2000 | Smith |
| 6,174,303 | B1 | 1/2001 | Suprise et al. |
| 6,192,521 | B1 | 2/2001 | Alberts et al. |
| 6,231,554 | B1 | 5/2001 | Menard |
| 6,240,569 | B1 | 6/2001 | Gompel et al. |
| 6,355,330 | B1 | 3/2002 | Koslow et al. |
| 6,381,994 | B1 | 5/2002 | Lee |
| 6,383,960 | B1 | 5/2002 | Everett et al. |
| 6,569,139 | B1 | 5/2003 | Datta et al. |
| 6,610,901 | B2 | 8/2003 | McMahon-Ayerst et al. |
| 6,622,312 | B2 | 9/2003 | Rabinowicz |
| 6,626,883 | B2 | 9/2003 | Wada et al. |
| 6,807,685 | B1 | 10/2004 | Hasegawa et al. |
| 6,848,121 | B1 | 2/2005 | Halid |
| 6,861,520 | B1 | 3/2005 | Todd et al. |
| 7,008,887 | B2 | 3/2006 | Rearick et al. |
| 7,083,604 | B2 | 8/2006 | Sakaguchi |
| 7,156,828 | B2 | 1/2007 | Ostrow |
| RE39,919 | E | 11/2007 | Dodge et al. |
| 7,322,966 | B1 | 1/2008 | Deerin |
| 7,393,346 | B2 | 7/2008 | Mormann et al. |
| 7,686,794 | B2 | 3/2010 | Mitchell |
| 7,951,128 | B1 | 5/2011 | Lewis |
| 8,052,665 | B2 | 11/2011 | Wastlund-Karlsson et al. |
| 8,058,343 | B2 | 11/2011 | Liu et al. |
| 8,117,675 | B2 | 2/2012 | Strange et al. |
| 8,282,618 | B2 | 10/2012 | Nordness et al. |
| 8,460,265 | B1 | 6/2013 | Calender |
| D701,018 | S | 3/2014 | Wexler |
| D716,020 | S | 10/2014 | Dunbar et al. |
| 8,935,813 | B2 | 1/2015 | O'Leary |
| 9,011,398 | B2 | 4/2015 | Johnston et al. |
| 9,301,551 | B2 | 4/2016 | Back et al. |
| 10,226,388 | B2 | 3/2019 | Nelson |
| 10,335,325 | B2 | 7/2019 | Sheldon et al. |
| 10,441,479 | B2 | 10/2019 | Griffiths |
| 10,441,480 | B2 | 10/2019 | Griffiths |
| 10,575,573 | B2 | 3/2020 | Griffiths |
| 10,765,564 | B2 | 9/2020 | Lee et al. |
| 10,897,941 | B1 | 1/2021 | Smoter |
| 10,905,596 | B2 | 2/2021 | Sina et al. |
| 11,154,431 | B1 | 10/2021 | Mp et al. |
| 11,207,225 | B2 | 12/2021 | Kajanthan et al. |
| 11,253,017 | B2 | 2/2022 | Friedrich |
| D948,167 | S | 4/2022 | Carpenter et al. |
| 11,331,229 | B2 | 5/2022 | Lee et al. |
| 11,395,774 | B2 | 7/2022 | Skinner et al. |
| 11,497,263 | B1 | 11/2022 | Deshaies et al. |
| 11,553,739 | B2 | 1/2023 | Henry |
| 11,576,826 | B2 * | 2/2023 | Fukae .................. A61F 13/515 |
| 11,590,034 | B2 | 2/2023 | Deshaies et al. |
| 11,701,267 | B2 | 7/2023 | Greco et al. |
| 2001/0031957 | A1 | 10/2001 | Prestley et al. |
| 2002/0016580 | A1 | 2/2002 | Wada et al. |
| 2002/0129434 | A1 | 9/2002 | Rabinowicz |
| 2002/0177829 | A1 | 11/2002 | Fell et al. |
| 2003/0004488 | A1 | 1/2003 | Ashton et al. |
| 2003/0124927 | A1 | 7/2003 | Waldroup et al. |
| 2003/0143376 | A1 | 7/2003 | Toyoshima et al. |
| 2003/0229933 | A1 * | 12/2003 | Nelson ...................... A61F 5/48 |
| | | | 2/406 |
| 2004/0229008 | A1 | 11/2004 | Hoying |
| 2004/0265533 | A1 | 12/2004 | Hoying et al. |
| 2005/0055002 | A1 | 3/2005 | Whitelaw et al. |
| 2005/0055005 | A1 | 3/2005 | Cazzato et al. |
| 2005/0090790 | A1 | 4/2005 | Veith |
| 2005/0131365 | A1 | 6/2005 | Sakaguchi |
| 2005/0197643 | A1 | 9/2005 | Suga et al. |
| 2006/0070163 | A1 | 4/2006 | Beck et al. |
| 2006/0247599 | A1 * | 11/2006 | Mullen ................. A61F 13/496 |
| | | | 604/402 |
| 2008/0108962 | A1 | 5/2008 | Furuta et al. |
| 2008/0110775 | A1 | 5/2008 | Beck et al. |
| 2008/0222781 | A1 | 9/2008 | Rhew |
| 2008/0275415 | A1 | 11/2008 | Wheeler et al. |
| 2008/0276352 | A1 | 11/2008 | Strange et al. |
| 2009/0240224 | A1 | 9/2009 | Underhill et al. |
| 2009/0247977 | A1 | 10/2009 | Takeuchi et al. |
| 2010/0222759 | A1 | 9/2010 | Hammons et al. |
| 2010/0249736 | A1 | 9/2010 | Png et al. |
| 2011/0048077 | A1 | 3/2011 | Warren et al. |
| 2011/0172621 | A1 | 7/2011 | Lee et al. |
| 2011/0224639 | A1 | 9/2011 | Venable |
| 2012/0123377 | A1 | 5/2012 | Back |
| 2013/0006209 | A1 | 1/2013 | Ruiz |
| 2013/0072888 | A1 | 3/2013 | Zorin |
| 2013/0125293 | A1 | 5/2013 | Stearns |
| 2014/0018763 | A1 * | 1/2014 | Evenson ........... A61F 13/49006 |
| | | | 604/385.14 |
| 2014/0039432 | A1 | 2/2014 | Dunbar et al. |
| 2014/0378935 | A1 | 12/2014 | Arayama et al. |
| 2016/0089276 | A1 | 3/2016 | Griffiths |
| 2016/0184146 | A1 | 6/2016 | Tulk et al. |
| 2016/0302979 | A1 | 10/2016 | Nelson et al. |
| 2017/0231836 | A1 * | 8/2017 | Manabe ........... A61F 13/49453 |
| | | | 604/385.27 |
| 2018/0014983 | A1 | 1/2018 | Jayasuriya et al. |
| 2019/0380886 | A1 | 12/2019 | Hammond |
| 2020/0000155 | A1 | 1/2020 | Etienne |
| 2020/0000649 | A1 | 1/2020 | Griffiths |
| 2020/0154790 | A1 | 5/2020 | Cleary |
| 2020/0222256 | A1 | 7/2020 | Chong |

(56) References Cited

U.S. PATENT DOCUMENTS

| | | | |
|---|---|---|---|
| 2021/0015684 A1 | | 1/2021 | Nakabugo |
| 2021/0030605 A1 | | 2/2021 | Kajanthan et al. |
| 2021/0100698 A1 | | 4/2021 | Langdon et al. |
| 2021/0177676 A1 | | 6/2021 | Kajanthan et al. |
| 2021/0282469 A1 | | 9/2021 | Siriwardena |
| 2021/0290447 A1 | | 9/2021 | Sepello et al. |
| 2021/0298369 A1 | | 9/2021 | Polstein et al. |
| 2022/0117790 A1 | | 4/2022 | Locke et al. |
| 2022/0117792 A1 | | 4/2022 | Bradford |
| 2022/0133544 A1 | | 5/2022 | Turton et al. |
| 2022/0142827 A1 | * | 5/2022 | Yip ........................ A41B 9/004 |
| 2022/0160552 A1 | | 5/2022 | Carpenter |
| 2022/0211558 A1 | | 7/2022 | Kajanthan et al. |
| 2022/0249303 A1 | | 8/2022 | Yang |
| 2022/0256938 A1 | | 8/2022 | King |
| 2022/0354710 A1 | | 11/2022 | Sepello et al. |
| 2022/0408848 A1 | | 12/2022 | Krupa |
| 2023/0010999 A1 | | 1/2023 | Sieck et al. |
| 2023/0012670 A1 | * | 1/2023 | Deshaies ............... A61F 13/505 |
| 2023/0128088 A1 | | 4/2023 | Deshaies et al. |
| 2023/0129586 A1 | | 4/2023 | Greco et al. |
| 2023/0225437 A1 | | 7/2023 | Carlino et al. |
| 2023/0338206 A1 | * | 10/2023 | Welch .................. A41D 31/102 |
| 2024/0032609 A1 | | 2/2024 | Power et al. |
| 2024/0164957 A1 | * | 5/2024 | Dushyantha ............ A61F 13/42 |

FOREIGN PATENT DOCUMENTS

| | | | |
|---|---|---|---|
| CA | 2126280 A1 | 12/1994 | |
| CA | 2126281 A1 | 12/1994 | |
| CA | 2152135 A1 | 12/1995 | |
| EP | 1370161 A1 | 12/2003 | |
| EP | 2725933 * | 7/2017 | ............. A41D 10/00 |
| EP | 3437604 A1 | 2/2019 | |
| EP | 4115859 * | 1/2023 | ............. A61F 13/15 |
| JP | 2005154922 A | 6/2005 | |
| JP | 2005154924 A | 6/2005 | |
| KR | 20070018490 A | 2/2007 | |
| KR | 100694187 B1 | 3/2007 | |
| WO | 1997046198 A1 | 12/1997 | |
| WO | 98/44883 * | 10/1998 | ............. A61F 13/15 |
| WO | 1998044883 | 10/1998 | |
| WO | WO-9844883 A1 * | 10/1998 | ............... A41D 7/00 |
| WO | 2006036841 A1 | 4/2006 | |
| WO | 2021160627 A1 | 8/2021 | |
| WO | 2023/057075 * | 4/2023 | ........... A61F 13/511 |
| WO | 2024012672 A1 | 1/2024 | |
| WO | WO2024107104 A1 | 5/2024 | |

OTHER PUBLICATIONS

Photographs of TomboyX Leakproof Bikini—Plum, ordered Nov. 10, 2020.

Photographs of SPEAX by Thinx Hiphugger Women's Underwear—Leakproof, Breathable—M—Beige, ordered Feb. 7, 2020.

Photographs of Ruby /Love Period Underwear Bikini—Pretty In Pink, ordered May 6, 2021.

"Bemis SewFree" webpage (www.bemisheatseal.com/Sewfree. htm), 2 pages, available at least as early as Aug. 4, 2001, retrieved from Internet Archive Wayback Machine (https://web.archive.org/web/20010804041402/http://www.bemisheatseal.com:%2080/Sewfree. htm) on Jan. 29, 2021.

Lo, T.Y., "Techtextil/Avantex 2005 (2)" Textile Asia, 2005, pp. 26-27.

Isaacs, Mac, "Seamless: Eliminating Stitches—More Than a Buzzword," AATCC Review, Nov. 2005, pp. 16-19.

Bemis Associates, Sewfree Adhesive Films for Intimate Apparel, 2013, 8 pages.

Photographs of Adidas Techfit Period-Proof Biker Short Tights, ordered Jun. 24, 2021.

Photographs Lilova Seamless High Waist, ordered Oct. 12, 2021.

Photographs Lilova Swimwear One-Piece Classic, ordered Oct. 12, 2021.

Photographs of Modibodi Seamfree Bikini Moderate-Heavy, ordered Feb. 9, 2022.

Photographs of Proof Leakproof Hipster Underwear, ordered Aug. 7, 2020.

Photographs of Pure Rosy Banded Brief—Jam, ordered Oct. 12, 2021.

Photographs of Neiwai Pantie Pro Low Waist Period Brief, purchased Dec. 11, 2023.

European Intellectual Property Office, Extended European Search Report, dated May 30, 2025, in EP25153297, which is a European application that claims priority to this U.S. application.

* cited by examiner

MOISTURE LOCK FLUID RETENTION ASSEMBLIES, GARMENTS INCLUDING THE SAME, AND RELATED METHODS

FIELD

The present disclosure relates to moisture lock fluid retention assemblies, garments including the same, and related methods.

BACKGROUND

Garments and other wearable accessories that are configured to be worn adjacent to a wearer's skin sometimes exhibit fluid and moisture-absorbing properties, such as to absorb and/or retain fluids produced by the user. For example, underwear garments and other wearable accessories have been configured to be worn adjacent to a wearer's crotch, or pelvic region, and that include fluid- or liquid-absorbing properties, such as to absorb and/or retain menstrual fluids, sweat, and/or urine excreted by the user. Wearers generally desire that such garments absorb and retain such fluids in a discreet and leakproof manner, such as to hide such fluids from view by outside observers and/or to enhance the wearer's comfort. These garments may be referred to as "period underwear," or "incontinence underwear." However, many such garments include absorbent regions that are bulky, uncomfortable, and/or difficult to conceal. To address these considerations, several prior art undergarments include absorbent regions that are bonded and/or laminated to a main body portion of the undergarment, though this bonding typically extends along the leg opening, which can be disadvantageous for certain manufacturing techniques. Additionally, even absorbent regions that are bonded to the garment typically include seams through the absorbent region to secure multiple layers of the absorbent region together, yet seams are a typical location of first leaks in absorbent garments. Thus, the overall absorbency of such prior art garments is often limited by side leaks through the edges of the absorbent region.

SUMMARY

Presently disclosed fluid retention assemblies, garments including the same, and related methods may allow for leakproof or leak-resistant cut-and-sew garments to be provided with absorbent regions that need not extend to and/or be bonded along the leg openings of the garment. Additionally or alternatively, the absorbent regions of disclosed fluid retention assemblies may be coupled to the garment base without seams through the absorbent region, thereby preventing or reducing side leaks and creating a more absorbent or leakproof garment as compared to prior art garments, without increasing bulk.

An example of disclosed garments generally may include a garment base and a fluid retention assembly. The garment base includes a garment base interior side and a garment base exterior side, with the garment base interior side configured to face the wearer when the garment is worn by the wearer, and the garment base exterior side configured to face outwardly away from the wearer when the garment is worn by the wearer. The fluid retention assembly is coupled to the garment base interior side and includes an outer perimeter, along with an assembly interior side that is configured to face the wearer when the garment is worn by the wearer and an assembly exterior side that is configured to face outwardly away from the wearer when the garment is worn by the wearer. The assembly exterior side faces the garment base interior side. Fluid retention assemblies of disclosed garments include an absorbent layer configured to absorb fluid excreted from the wearer when the garment is worn. The absorbent layer is defined by an absorbent layer interior side that is configured to face the wearer when the garment is worn by the wearer, and an absorbent layer exterior side that is configured to face outwardly away from the wearer when the garment is worn by the wearer. Fluid retention assemblies of disclosed garments also include a moisture-impermeable layer that underlies the absorbent layer and separates the garment base interior side from the absorbent layer exterior side. The moisture-impermeable layer is substantially impermeable to moistures and fluids, such that it is configured to restrict fluid from exiting the fluid retention assembly to the garment base interior side. The moisture-impermeable layer extends to and wraps around at least a portion of the outer perimeter of the fluid retention assembly such that it (e.g., the portion of the moisture-impermeable layer that wraps around the outer perimeter) may be coupled to the assembly interior side.

An example of disclosed fluid retention assemblies may include an absorbent layer configured to absorb fluid excreted from the wearer when the fluid retention assembly is in use, and a moisture-impermeable layer that underlies the absorbent layer, wherein the moisture-impermeable layer is configured to restrict fluid from exiting the fluid retention assembly once absorbed by the absorbent layer. The moisture-impermeable layer may extend to and wraps around at least a portion of an outer perimeter of the fluid retention assembly and is coupled to the assembly interior side. The absorbent layer may include an absorbent-layer interior side that is configured to face the wearer when the fluid retention assembly is in use, and an absorbent-layer exterior side that is configured to face outwardly away from the wearer when the fluid retention assembly is in use. An assembly interior side of the fluid retention assembly may be configured to face the wearer when the fluid retention assembly is in use, and an assembly exterior side of the fluid retention assembly may be configured to face outwardly away from the wearer when the fluid retention assembly is in use.

Methods of manufacturing absorbent garments are also within the scope of the present disclosure. Methods generally include forming the fluid retention assembly and coupling the fluid retention assembly to the garment base interior side of the garment base. Forming the fluid retention assembly generally includes wrapping the moisture-impermeable layer around at least a portion of the outer perimeter of the fluid retention assembly, such that the moisture-impermeable layer may be configured to form a moisture lock around he absorbent layer of the fluid retention assembly. Coupling the fluid retention assembly to the garment base may include bonding one or more bonding tapes to the fluid retention assembly and sewing or stitching the bonding tapes to the garment base without sewing or stitching through the fluid retention assembly itself.

DESCRIPTION

Figure 1:
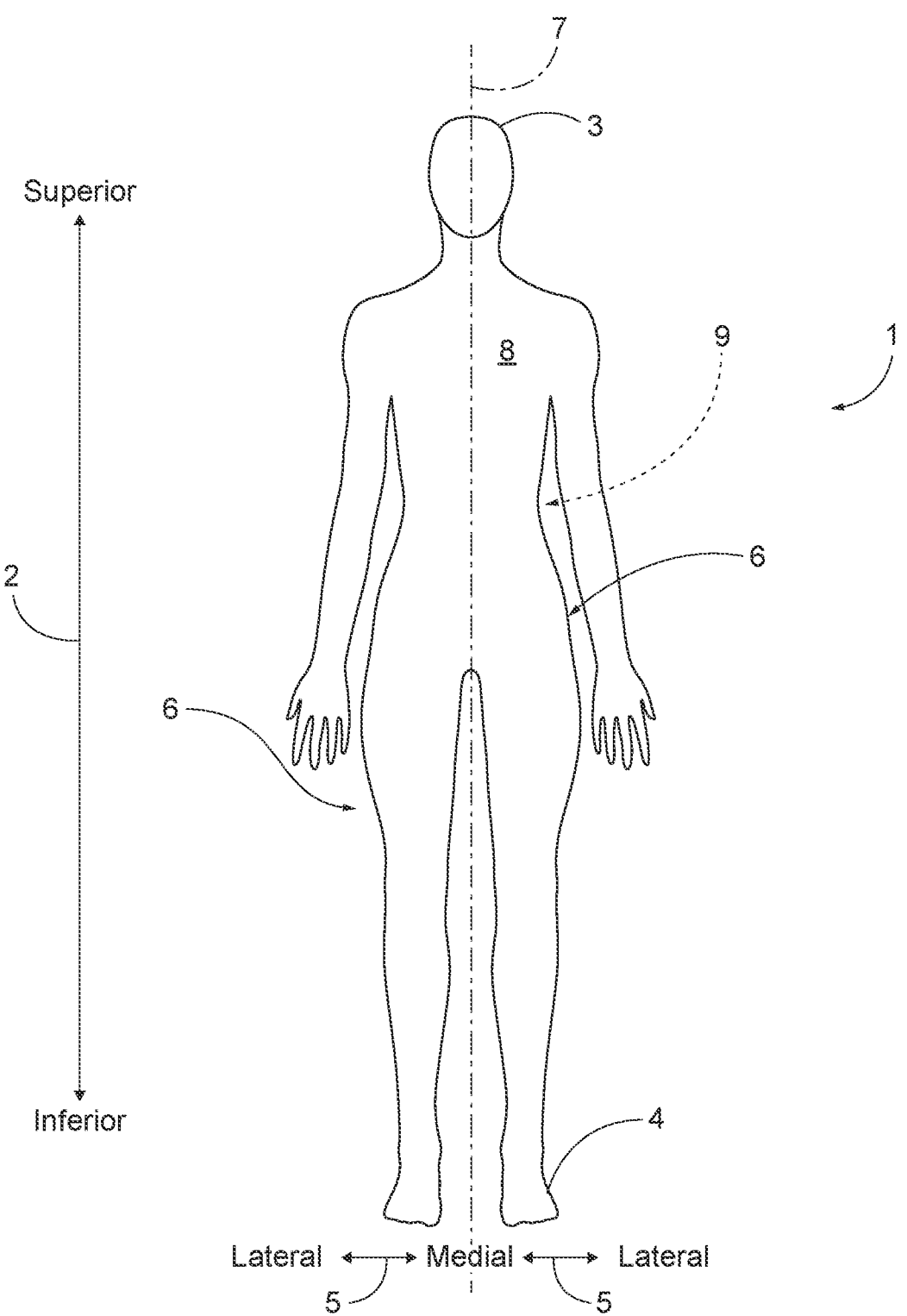
FIG. 1 is a representation of a generic human figure, providing reference direction indications for use in the specification.

FIG. 1 provides a general reference framework for discussion of presently disclosed garments and fluid retention assemblies, with reference to a wearer 1. As indicated by arrow 2, a first component or feature of the disclosed garments or fluid retention assemblies may be described as being superior relative to another component or feature, or relative to an aspect of wearer 1, if the first component or feature is closer to the head 3 of wearer 1. Similarly, a first component or feature of the disclosed garments or fluid retention assemblies may be described as being inferior relative to another component or feature, or relative to an aspect of wearer 1, if the first component or feature is closer to the feet 4 of wearer 1.

As indicated by arrows 5, a first component or feature of the disclosed garments or fluid retention assemblies may be described as being lateral to another component or feature, or to an aspect of wearer 1, if the first component or feature is closer to a side 6 of wearer 1 than is the other component or feature. Likewise, a first component or feature of the disclosed garments or fluid retention assemblies may be described as being medial to another component or feature, or to an aspect of wearer 1, if the first component or feature is closer to an imaginary centerline 7 of wearer 1 than the other component or feature. Put another way, a first component or feature is medial to a second component or feature if the first component or feature is closer to imaginary centerline 7 than the second component or feature is, whereas a first component or feature is lateral to a second component or feature if the first component or feature is closer to a given side 6 than is the second component or feature. Thus, generally, if a first component or feature is lateral to a second component or feature, then the second component or feature will likewise be medial to the first component or feature.

Components or features of disclosed garments or fluid retention assemblies also may be described relative to an anterior side and a posterior side of the garments. As used herein, the anterior side of garments, fluid retention assemblies, or components thereof refers to the side that is configured to be positioned on or relatively nearer to the wearer's anterior side 8 (e.g., the front half of the wearer's body) when the garment is worn or when the fluid retention assembly is in use. Similarly, the posterior side of garments or components refers to the side that is configured to be positioned on or relatively nearer to the wearer's posterior side 9 (e.g., the back half of the wearer's body). Additionally or alternatively, components or features of disclosed garments or fluid retention assemblies may be described in terms of being anterior or posterior relative to each other when one component or feature is closer to the anterior or posterior side of the garment or fluid retention assembly than the other.

As represented in FIG. 1 and as described herein, the various elements of garments or fluid retention assemblies disclosed herein may be described in terms of relative positions to each other when such garments are worn, or donned, by a wearer, or when the fluid retention assembly is in use, when the wearer is standing vertically, and from the perspective of the wearer. Such terms may include terms such as "above," "below," "upper," "lower," "front," "back," "behind," "under," and similar. Accordingly, when describing a first element as being above or below a second element, the first element falls in a horizontal plane that is above or below a horizontal plane in which the second element falls, but the first element is not necessarily directly above or below the second element along a vertical vector.

Furthermore, an "edge" of an element of disclosed garments, as used herein, additionally or alternatively may be referred to as, or described as, an edge region, a margin, or a boundary of the element, and an "edge" is not necessarily the absolute two-dimensional terminus of the element. For example, as typical in garment construction, seams may have a width to them, and the region associated with a seam may be considered the "edge" of the element. Moreover, two panels or sections of material being secured together at a seam often are not perfectly aligned along their terminuses. Moreover, a seam within an expanse of material may define an "edge" of a sub-portion of that expanse of material, with the sub-portion optionally being described as a "panel" or "region" of the material. In other words, two adjacent panels or regions may, in some cases, be constructed of the same piece of material with a seam or other structure defining an edge, or boundary, between the two adjacent panels.

FIGS. 2-3, 8-9, and 11-12 provide schematic representations of non-exclusive examples of garments 10 and/or fluid retention assemblies 14, or potential components or aspects thereof, according to the present disclosure. Elements that serve a similar, or at least substantially similar, purpose are labeled with like numbers in each of FIGS. 2-3, 8-9, and 11-12, and these elements may not be discussed in detail herein with reference to each of FIGS. 2-3, 8-9, and 11-12. Similarly, all elements may not be labeled in each of FIGS. 2-3, 8-9, and 11-12, but reference numerals associated therewith may be utilized herein for consistency. Elements, components, and/or features that are discussed herein with reference to one or more of FIGS. 2-3, 8-9, and 11-12 may be included in and/or utilized with any of FIGS. 2-3, 8-9, and 11-12 without departing from the scope of the present disclosure. In general, elements that are likely to be included in a given (i.e., a particular) example are illustrated in solid lines, while elements that are optional to a given example are illustrated in dashed lines. However, elements that are shown in solid lines are not essential to all examples, and an element shown in solid lines may be omitted from a particular example without departing from the scope of the present disclosure.

Figure 2:
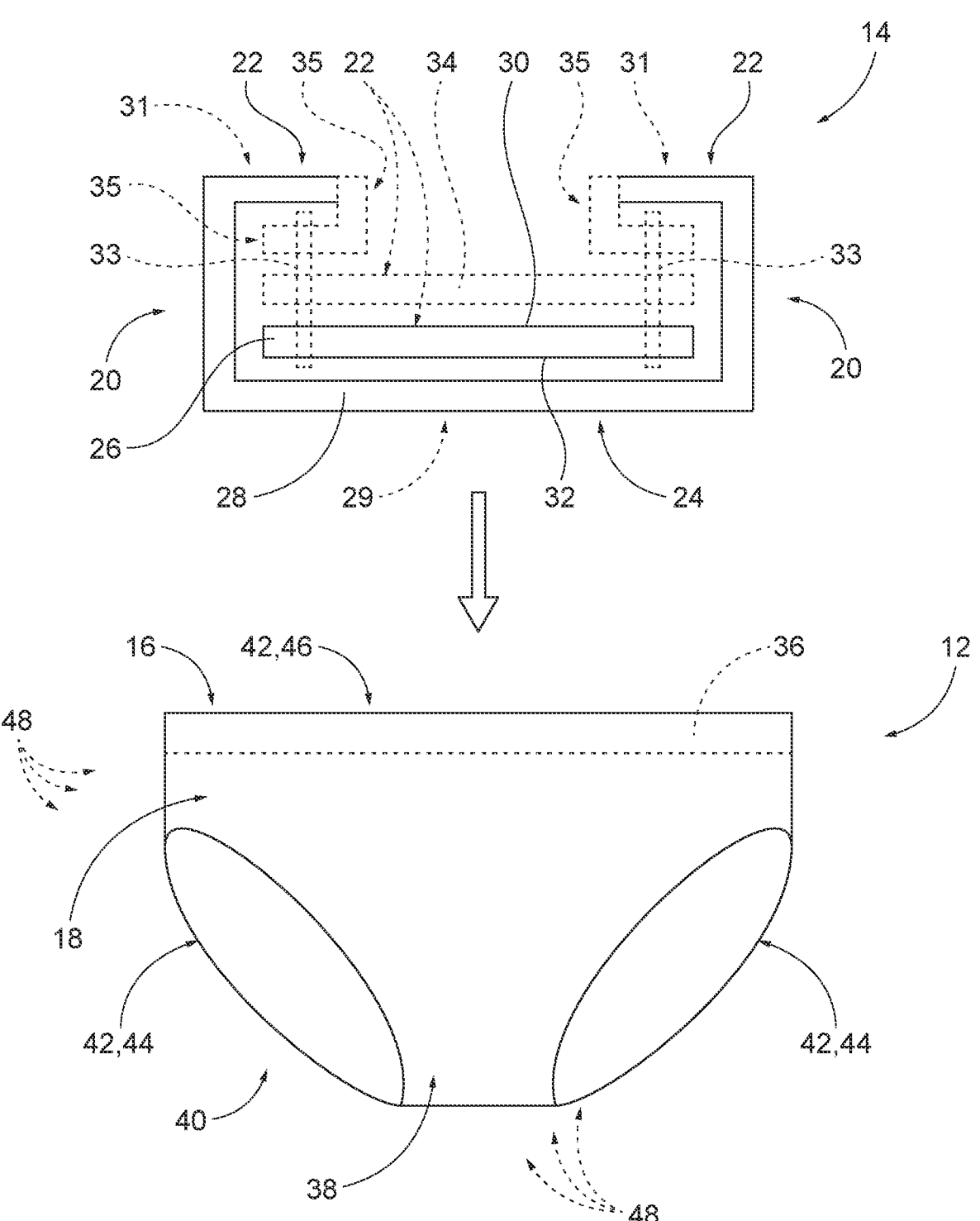
FIG. 2 is an exploded schematic representation of examples of garments according to the present disclosure, shown from the front of the garment.

FIG. 2 is a schematic exploded representation of illustrative examples of garments 10 according to the present disclosure. While garment 10 is represented in FIG. 2 as a lower body garment, garments 10 according to the present disclosure may include upper body garments (e.g., tops, shirts, sweaters, sweatshirts, bras, sports bras etc.); lower body garments (e.g., bottoms, shorts, tights, leggings, hosiery, pants, skorts, skirts, underwear, briefs, swim bottoms, etc.); undergarments (e.g., briefs, panties, boxers, boy shorts, etc.); full body garments (e.g., rompers, dresses, jumpsuits, onesies, swimsuits, etc.); or other types of garments or wearable accessories (e.g., hats, scarves, neck gaiters, sweat bands, etc.). Garments 10 may be configured to be worn as outer wear, or as undergarments. Garments 10 may be configured as activewear garments, intended be worn while exercising or participating in physical activity. Garments 10 generally are configured to be machine-washable and re-worn numerous times.

Garments 10 generally include a garment base 12 and fluid retention assembly 14, which is schematically represented in cross-section in FIG. 2 for illustrative purposes, and is not drawn to scale. Garment base 12 has an interior side 16 (also referred to herein as garment base interior side 16) and an exterior side 18 (also referred to herein as garment base exterior side 18), with interior side 16 being configured to face the wearer when garment 10 is worn by the wearer, and exterior side 18 being configured to face outwardly away from the wearer when garment 10 is worn. In particular, in some examples, at least a portion of the garment base interior side 16 is configured to directly contact the wearer's skin when garment 10 is worn by the wearer. Stated differently, in some examples, garment 10 is configured such that, when garment 10 is worn by the wearer, no portion of garment 10 is positioned directly between the garment's interior side 16 and the wearer's body in at least some areas of garment 10. Similarly, in some examples, garment 10 is configured such that, when the garment is worn by the wearer, no portion of the garment is positioned distal the wearer relative to the garment's exterior side 18.

Fluid retention assembly 14 defines an outer perimeter 20 and is coupled to interior side 16 of garment base 12. Fluid retention assembly 14 includes an assembly interior side 22 that is configured to face the wearer when garment 10 is worn. For example, assembly interior side 22 may be configured to contact the wearer's skin, may be placed adjacent to the wearer's body when garment 10 is worn, and/or may be nearer to the wearer's body when garment 10 is worn than is an assembly exterior side 24 of fluid retention assembly 14. Thus, assembly exterior side 24 may be configured to face outwardly away from the wearer when garment 10 is worn. Assembly exterior side 24 generally faces and/or contacts interior side 16 of garment base 12 when fluid retention assembly 14 is coupled to garment base 12, while assembly interior side 22 and garment base interior side 16 face and/or contact the wearer's skin when garment 10 is worn.

Fluid retention assembly 14 may have any of a variety of constructions, and is configured for absorbing and capturing fluids, liquids, or moisture from the wearer, and then retaining the captured fluids to at least substantially prevent them from leaking into other areas of garment 10 and/or the wearer's other clothing. Fluid retention assembly 14 includes at least an absorbent layer 26 configured to absorb fluid excreted from the wearer when garment 10 is worn, and a moisture-impermeable layer 28 configured to restrict passage of liquid therethrough and/or restrict fluid from exiting fluid retention assembly 14 to garment base interior side 16. Absorbent layer 26 includes an absorbent layer interior side 30 that is configured to face the wearer when garment 10 is worn by the wearer, and an absorbent layer exterior side 32 that is configured to face outwardly away from the wearer when garment 10 is worn by the wearer. At least a portion of moisture-impermeable layer 28 underlies absorbent layer 26 (e.g., may be positioned adjacent absorbent layer exterior side 32) and separates garment base interior side 16 from absorbent layer exterior side 32 when fluid retention assembly 14 is coupled to garment base 12.

The layers of fluid retention assembly 14 are illustrated in a partially exploded, spaced apart fashion in FIG. 2 for clarity, though generally, adjacent layers of fluid retention assembly 14 will be in contact with one another.

Further, moisture-impermeable layer 28 extends to and wraps around (e.g., folds over) at least a portion of outer perimeter 20 of fluid retention assembly 14 such that a portion 31 of moisture-impermeable layer 28 may form a portion of assembly interior side 22 and be coupled to one or more other layers of fluid retention assembly 14 that form assembly interior side 22 (which may correspond to or be formed by, for example, absorbent layer interior side 30 or a moisture-wicking layer 34). Portion 31 may also be referred to herein as folded over portion 31. This construction may be configured to advantageously prevent or reduce side leaks along outer perimeter 20, thereby addressing a common disadvantage of prior art garments (in which leakage through side edges commonly limits the overall absorbency of the prior art garment). While one or more layers of fluid retention assembly 14 may be sewn together around some or all of outer perimeter 20 in some examples (e.g., via serging, sewing, or stitching indicated at 33), moisture-impermeable layer 28 may effectively encase, or cover, any such seams or stitching 33 where moisture-impermeable layer 28 wraps around outer perimeter 20. For example, moisture-impermeable layer 28 may be folded back under itself where it folds around the outer perimeter 20 of fluid retention assembly 14, to form a folded under portion 35. In this manner, moisture-impermeable layer 28 itself (e.g., folded over portion 31 of moisture-impermeable layer 28) may effectively surround the edges of the other layers of fluid retention assembly 14, such that the folded over portions 31 of moisture-impermeable layer 28 are not penetrated by any stitching or sewing 33 coupling layers 26, 28, and/or 34 of fluid retention assembly 14 together.

As shown in FIG. 2, absorbent layer 26, moisture wicking layer 34, and/or folded under portion 35 of moisture-impermeable layer 28 may be directly coupled together around at least a portion of outer perimeter 20 via seam or stitching 33 extending through absorbent layer 26, moisture-wicking layer 34, and/or folded under portion 35 of moisture-impermeable layer 28. Folded under portion 35 of moisture-impermeable layer 28 thus may be secured to absorbent layer 26 and/or moisture-wicking layer 34 via seam or stitching 33, while seam or stitching 33 does not penetrate portion 31 of moisture-impermeable layer 28 that folds over onto assembly interior side 22 of fluid retention assembly 14. In other examples of fluid retention assembly 14, moisture-impermeable layer 28 may fold over outer perimeter 20 at portion 31, without folding back over onto itself to form folded under portion 35. To construct disclosed fluid retention assemblies 14, the layers 26, 28, and/or 34 may be sewn together inside-out, and then flipped right side out. In some examples, disclosed fluid retention assemblies 14 are constructed without any adhesive or bonding between absorbent layer 26, moisture-wicking layer 34, and moisture-impermeable layer 28. In some examples, layers 26, 28, and/or 34 are sewn together along opposing lateral edges 50 of outer perimeter 20, while layers 26, 28, and/or 34 are bonded together (e.g., via bonding tape) along anterior edge 52 and/or a posterior edge 54 of outer perimeter 20.

Moisture-impermeable layer 28 (which may include one or a plurality of moisture-impermeable layers) is positioned with respect to garment base 12 such that moisture-impermeable layer 28 separates interior side 16 of garment base 12 from absorbent layer 26 (which may include one or a plurality of absorbent layers). In this manner, moisture-impermeable layer 28 is configured to restrict and/or at least substantially prevent fluid from passing through and exiting fluid retention assembly 14 to interior side 16 and exterior side 18 of garment base 12. In other words, fluid retention assembly 14 may be configured to retain fluids excreted by the wearer (e.g., within absorbent layer 26), and restrict or prevent them from soaking through to garment base 12, thereby allowing garment 10 to be configured as a leak-proof or leak-resistant garment in areas corresponding to fluid retention assembly 14. In some examples, a portion 29 of moisture-impermeable layer 28 defines assembly exterior side 24 of fluid retention assembly 14 and/or forms the outermost layer of at least a portion of fluid retention assembly 14, such that that portion 29 of moisture-impermeable layer 28 contacts garment base interior side 16 when garment 10 is worn. In other examples, assembly exterior side 24 of fluid retention assembly 14 may be defined by an external layer configured to sandwich the one or more moisture-impermeable layers 28 between the external layer and absorbent layer 26. Furthermore, portion 31 of moisture-impermeable layer 28 may define some of assembly interior side 22 of fluid retention assembly 14, where moisture-impermeable layer 28 wraps around outer perimeter 20 of fluid retention assembly 14, thereby creating a moisture lock around absorbent layer 26. However, in some examples, moisture-impermeable layer 28 is only coupled on assembly interior side 22 of fluid retention assembly 14 along some of outer perimeter 20, such as along opposing lateral edges 50 (FIG. 3) of outer perimeter 20. As used herein, a feature may be said to be positioned "along" or coupled "along" a perimeter, a seam, an aperture, or the like, if the feature substantially follows the contour of the perimeter, the seam, the aperture, or the like.

In examples of fluid retention assembly 14 that include moisture-wicking layer 34, moisture-wicking layer 34 may be configured to be positioned against the wearer's skin when garment 10 is worn, with absorbent layer 26 (or multiple absorbent layers 26) being sandwiched between moisture-wicking layer 34 and moisture-impermeable layer 28. In particular, in such examples, moisture-wicking layer 34 may be configured to draw moisture away from the wearer, such as via capillary action, and to direct and/or convey the moisture or fluids to fluid retention assembly 14. Moisture-wicking layer 34 may form some of, or at least substantially all of, assembly interior side 22 of fluid retention assembly 14. For example, moisture-wicking layer 34 may form all of assembly interior side 22 except where portion 31 of moisture-impermeable layer 28 wraps around outer perimeter 20 of fluid retention assembly 14. In some examples, moisture-impermeable layer 28, absorbent layer 26, and/or moisture-wicking layer 34 are not directly coupled together except along some or all of outer perimeter 20 of fluid retention assembly 14. For example, moisture-impermeable layer 28, absorbent layer 26, and moisture-wicking layer 34 may be coupled together via a seam or stitching along some or all of outer perimeter 20 (e.g., seam or stitching 33), with moisture-impermeable layer 28 effectively encasing or enclosing the seam or stitching in the areas where moisture-impermeable layer 28 wraps around outer perimeter 20. Additionally or alternatively, moisture-wicking layer 34 and absorbent layer 26 may be at least substantially co-extensive such that an outer edge of absorbent layer 26 substantially meets an outer edge of moisture-wicking layer 34.

Fluid retention assemblies 14 and garment base 12 according to the present disclosure may be formed of various suitable materials. Materials described herein are not limiting, and included only for illustrative purposes. For example, moisture-wicking layer 34 may be formed of materials or fabric formed from or including cotton, carbon cotton, carbon-cotton spandex, a synthetic fiber fabric, a natural fiber, polyester, nylon, modal, bamboo, Spandex™ fabric, and/or combinations thereof. Additionally or alternatively, moisture-wicking layer 34 may be formed from one or more materials selected to have quick-drying, odor fighting, and/or anti-microbial properties and/or may be treated or coated to achieve one or more of these properties. Moisture-wicking layer 34 may include a mesh material and/or a solid material. Absorbent layer 26 may be formed of a variety of materials, with examples including polyester nylon, natural fiber, cotton, a synthetic fiber, polyester, nylon, Spandex™ fabric, and/or other pulp-based fibers such as modal or bamboo, and/or combinations thereof. Absorbent layer 26 may be absorbent enough to absorb at least 2 teaspoons (10 ml), at least 3 teaspoons (15 ml), at least 4 teaspoons (20 ml), and/or at least 5 teaspoons (25 ml) of liquid or fluid excreted from the wearer of garment 10. Moisture-impermeable layer 28 may be a leak resistant, water resistant, or waterproof fabric or other moisture barrier material, a moisture barrier layer, a moisture barrier film, moisture barrier membrane, a waterproof, water-resistant, or water-repellant treatment, and/or a waterproof, water-resistant, or water-repellant coating. Garment base 12 may be formed from, for example, a fabric that is four-way stretch, lightweight, breathable, quick-drying, wicking, and/or odor-resistant, with suitable, non-limiting examples including natural fiber, cotton, a synthetic fiber, polyester, nylon, elastane (e.g., Spandex™ fabric), and/or combinations thereof. Garment base 12 may include one or more base layers, and/or may be a single continuous piece or may be formed of a plurality of base panels operatively coupled to one another, such as by stitching or sewing.

When garment 10 is worn, fluid retention assembly 14 is positioned in a region of garment 10 that is configured to be positioned on, adjacent to, and/or around a region of the wearer where fluids may be excreted. For example, fluid retention assembly 14 may be positioned in a region of garment 10 that is configured to be positioned on, adjacent to, and/or around the wearer's pelvic region when the garment is worn by the wearer. Additionally, fluid retention assembly 14 may be sized and shaped to effectively capture fluids excreted from the wearer when garment 10 is worn. In some examples, fluid retention assembly 14 has a length that is at least 6 inches (15 cm), at least 7 inches (17.8 cm), at least 8 inches (20 cm), at least 9 inches (22.8 cm), at least 10 inches (25.4 cm), at least 11 inches (28 cm), at least 12 inches (30.5 cm), at least 13 inches (33 cm), at least 14 inches (35.5 cm), and/or at most 15 inches (38 cm) long.

Garment 10 may include a waistband region 36, which may be at least partially defined by garment base 12. In some examples, fluid retention assembly 14 does not extend to waistband region 36 on an anterior side 38 of garment base 12 (which generally corresponds to the anterior side of garment 10) and/or on a posterior side 40 of garment base 12 (which generally corresponds to the posterior side of garment 10). Additionally or alternatively, in some examples fluid retention assembly 14 extends to waistband region 36 on anterior side 38 of garment base 12 and/or on posterior side 40 of garment base 12. In examples where fluid retention assembly 14 extends to waistband region 36 on anterior side 38 and/or posterior side 40 of garment base 12, fluid retention assembly 14 may be directly coupled to garment base 12 along waistband region. For example, anterior edge 52 of fluid retention assembly 14 may be coupled to garment base 12 along waistband region 36 on anterior side 38 of garment base 12, and/or posterior edge 54 of fluid retention assembly 14 may be coupled to garment base 12 along waistband region 36 on posterior side 40 of garment base 12.

In some examples, garment 10 (e.g., garment base 12) includes one or more garment apertures 42, such as one or more leg openings 44 and a waistband opening 46. Leg openings 44 are configured to receive a leg of the wearer therethrough when garment 10 is worn by the wearer. While FIG. 2 illustrates an example in which garment apertures 42, 44 are configured to receive a leg of the wearer when garment 10 is worn, garments 10 additionally or alternatively may include one or more garment apertures 42 that define an arm opening that is configured to receive an arm of the wearer when garment 10 is worn by the wearer, a neck opening configured to receive the wearer's head therethrough when garment 10 is worn, a waist opening configured to receive the wearer's torso or waist region when garment 10 is worn, or various other apertures that may be included in various types of garments 10.

Garment 10 may include one or more adhesive bonds 48 formed by an adhesive material that is applied to one or both of garment base 12 and fluid retention assembly 14. The adhesive material of one or more of any included adhesive bonds may be formed from, for example, one or more of a tape, an elastic tape, a film, an elastic film, a spray-on adhesive, and a thermoset adhesive. In some examples, the adhesive material of one or more of any included adhesive bonds 48 is water-resistant, water-repellent, and/or water-proof. In some examples, garment 10 includes one or more adhesive bonds 48 formed at least partially via a thermo-compression process. For example, adhesive bonds 48 may be positioned along one or more garment apertures 42, along waistband region 36, and/or along a portion of outer perimeter 20 of fluid retention assembly 14. However, some examples of garment 10 do not include adhesive bonds 48 in one, some, or any of these areas of garment 10. Presently disclosed garments 10 may be configured to be cut-and-sew garments, which was not attainable with conventional techniques and/or using certain materials due to the need to bond absorbent sections along leg openings. For example, certain materials such as cotton or other natural fibers may not be suitable for bonding. Presently disclosed garments 10 are configured to enable the construction of leak proof or leak-resistant cut-and-sew garments that may provide improved longevity and/or cost savings over bonded garments.

As noted above, garments 10 are not limited to lower body garments. In various types of garments 10 according to the present disclosure, one or more fluid retention assemblies 14 may be positioned in a region of garment 10 that is configured to be positioned on, adjacent to, and/or around the wearer's pelvic region (e.g., the wearer's crotch or groin region), armpit region, bra line region, torso region, back, shoulders, buttocks, legs, arms, chest, neck, nipples, and/or breast region when the garment is worn by the wearer. In specific examples, one or more fluid retention assemblies 14 are configured and positioned to absorb and retain various fluids excreted from the wearer or produced by the wearer while the wearer wears garment 10, such as urine, sweat, blood, menstrual fluids, excrement, breast milk, wound excretions, or other fluids. For example, fluid retention assembly 14 may be configured and positioned to address specific applications or uses of garment 10. For example, fluid may exit the body in different positions, or may flow in different directions after exiting the body, when a user is predominantly supine or bedridden, or when a user is predominantly in a seated position, than when the user is standing or moving around or engaged in physical activity. Depending on the user's position, fluid may flow forwards or backwards when it leaves the body, or may be centralized in a middle area of garment 10, and garments 10 may be specifically configured to absorb fluids in the direction they flow based on the intended user's predominant expected positioning. In another example, absorbency may be needed, for example, in areas of garment 10 configured to be positioned closest to the user's urethra or vagina, so garments 10 may be provided with fluid retention assembly 14 positioned in the desired relevant area of garment 10. In some examples, it may be desirable to have absorbency in the front of garment 10 (e.g., along anterior side 38) and/or in the back of garment 10 (e.g., along posterior side 40). To this end, fluid retention assembly 14 may be positioned, sized, and/or shaped differently in various different examples of garments 10 to address the specific needs and positioning created by different users and/or different body positions of the user while wearing garments 10. Additionally or alternatively, materials may be selected for absorbent layer 26 that wick the absorbed fluids in a desired direction. For example, materials may be selected for absorbent layer 26 that are configured to wick fluids predominantly horizontally (e.g., laterally towards lateral edges 50 of outer perimeter 20 of fluid retention assembly 14), or materials may be selected for absorbent layer 26 that are configured to wick fluids predominantly vertically (e.g., anteriorly towards anterior edge 52 and posteriorly towards posterior edge 54). Choosing materials that wick the fluid more vertically may further enhance leak-proof or leak-resistant performance along lateral edges 50 of fluid retention assembly 14.

Disclosed garments 10 may be configured to restrict such moisture or fluids from penetrating through garment 10 to reach interior side 16 and/or exterior side 18 of garment base 12. Fluid retention assemblies 14 thus may be positioned in various types of garments to prevent seepage or leakage of bodily excretions from being visible on exterior side 18 of garment base 12 or from seeping through to other items of clothing worn over garment 10. For example, one or more fluid retention assemblies 14 may be placed on a given garment 10 in locations where the wearer might otherwise have visible sweat when undergoing physical activity, and/or may be optimized for various types of incontinence or menstruation, and/or for absorbing breast milk leakage in nursing mothers. Other uses of disclosed fluid retention assemblies 14 also are within the scope of the present disclosure.

Disclosed fluid retention assemblies 14 may be provided independently from garments 10, as standalone units. Said fluid retention assemblies 14 may be configured to be integrated into an existing garment (e.g., retrofit), and may be compatible with a wide range of types and brands of garments. For example, isolated or standalone fluid retention assemblies 14 may be configured to be adhered to existing garments, sewn in to existing garments, and/or otherwise coupled to and/or positioned with respect to existing garments. The same size and shape of standalone fluid retention assembly 14 may be suitable to be incorporated into a variety of different types of garments, such as briefs, bikini bottoms, boy shorts, and etc. This may enable incorporating a high performing fluid retention assembly 14 into a lower cost garment to provide leak proof or leak resistant functionality in a garment with an overall lower manufacturing cost compared to prior art garments with comparable functionality.

Figure 3:
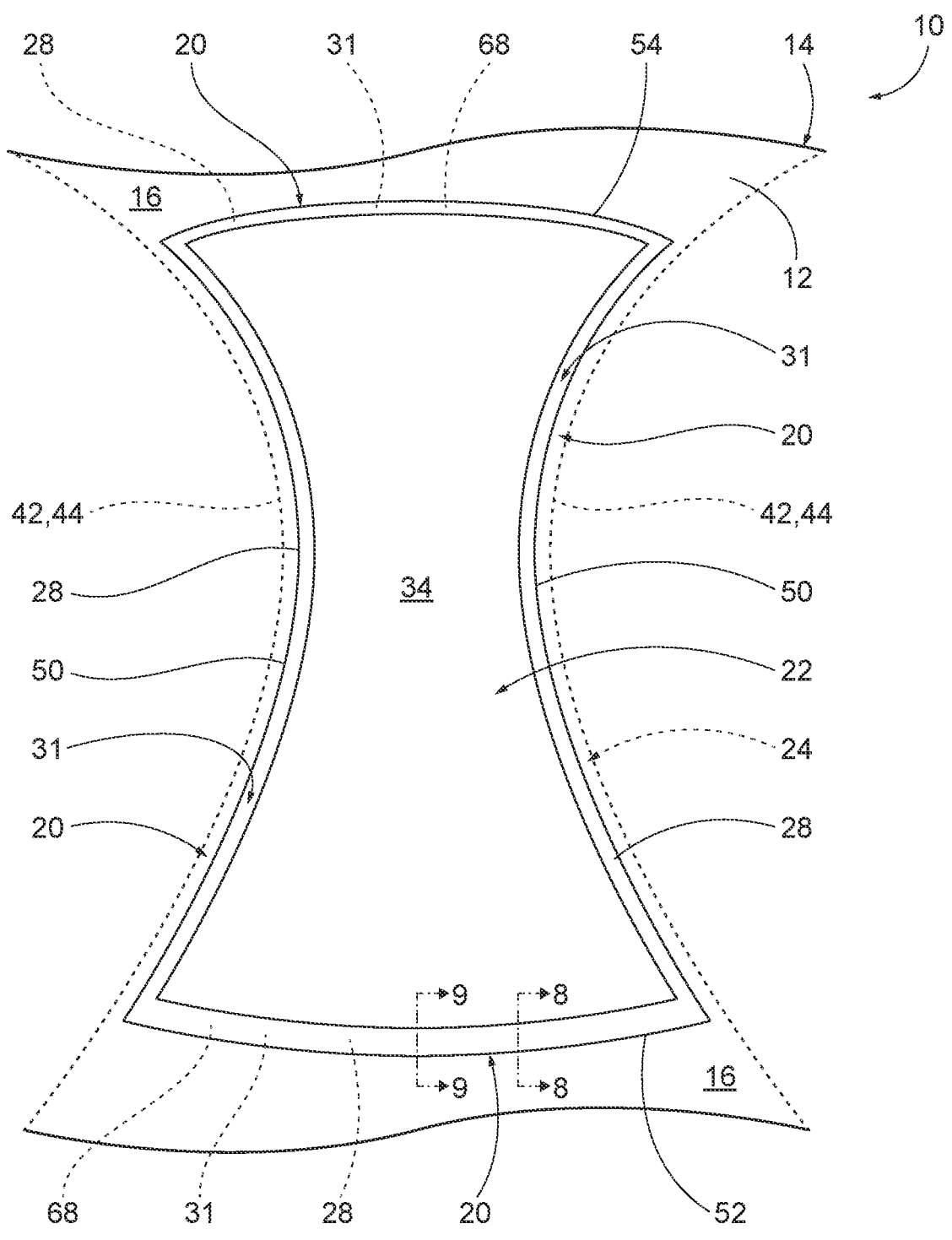
FIG. 3 is a schematic top plan view of examples of fluid retention assemblies according to the present disclosure.

FIG. 3 schematically illustrates an example of fluid retention assembly 14, viewed from the top and shown positioned with respect to a portion of garment base 12 (represented in dashed lines). As seen in FIG. 3, moisture-wicking layer 34 may form at least a portion of assembly interior side 22, and in some examples forms the entirety of assembly interior side 22 except along some or all of outer perimeter 20 where portion 31 of moisture-impermeable layer 28 is wrapped around outer perimeter 20 to assembly interior side 22. While the shape of outer perimeter 20 shown in FIG. 3 is not limiting, various examples of shapes of outer perimeter 20 may include opposing lateral edges 50, which, in some examples are positioned adjacent and/or along garment apertures 42, such as leg openings 44. Garment base 12 extends laterally beyond opposing lateral edges 50 of fluid retention assembly 14 in some examples. Put another way, fluid retention assembly 14 may be sized with respect to garment base 12 such that fluid retention assembly 14 extends laterally to a lesser extent than does garment base 12. In the example shown in FIG. 3, fluid retention assembly 14 is shown having an outer perimeter 20 that is configured for placement in a crotch region of garment 10, between garment apertures 42. While FIG. 3 shows garment apertures 42 near opposing lateral edges 50 of fluid retention assembly 14, other examples of garments 10 may have a larger gap or space between each respective opposing lateral edge 50 of fluid retention assembly 14 and each respective garment aperture 42. As shown in FIG. 3, moisture-impermeable layer 28 (e.g., portion 31 of moisture-impermeable layer 28) wraps around opposing lateral edges 50 of outer perimeter 20 of fluid retention assembly 14 in some examples. Additionally or alternatively, moisture-impermeable layer 28 may wrap around an anterior edge 52 and/or a posterior edge 54 of outer perimeter 20 of fluid retention assembly 14. In other words, in some examples, moisture-impermeable layer 28 may wrap around all or substantially all of outer perimeter 20, while in other examples, moisture-impermeable layer 28 may wrap around just a portion of outer perimeter 20.

Fluid retention assembly 14 is coupled to garment base interior side 16 of garment base 12, though as will be described in further detail herein, in some examples only a portion of fluid retention assembly 14 is directly coupled to garment base 12. For example, at least a substantial length (e.g., greater than 50% of the length) of opposing lateral edges 50 of outer perimeter 20 of fluid retention assembly 14 are not bonded, sewn, or otherwise directly coupled to garment base 12 in some examples of garment 10. In this sense, fluid retention assembly 14 may be said to be "floating" with respect to garment base 12 because a substantial portion of the footprint of fluid retention assembly 14 may be free from direct coupling to garment base 12. In various examples of garments 10, at least 50% of the length of opposing lateral edges 50 are not directly coupled to garment base 12, at least 60% of the length of opposing lateral edges 50 are not directly coupled to garment base 12, at least 70% of the length of opposing lateral edges 50 are not directly coupled to garment base 12, at least 80% of the length of opposing lateral edges 50 are not directly coupled to garment base 12, at least 90% of the length of opposing lateral edges 50 are not directly coupled to garment base 12, and/or at least 95% of the length of opposing lateral edges 50 are not directly coupled to garment base 12. In some examples, fluid retention assembly 14 is substantially only directly coupled to garment base 12 along or near anterior edge 52 and posterior edge 54 of outer perimeter 20 of fluid retention assembly 14. In some examples, no stitching or seams directly pass through fluid retention assembly 14 to couple fluid retention assembly 14 to garment base 12, thereby avoiding forming holes through fluid retention assembly 14 that could result in leaks. In other examples, no stitching or seams directly pass through fluid retention assembly 14 to couple fluid retention assembly 14 to garment base 12 along lateral edges 50 of outer perimeter 20, while posterior edge 54 and/or anterior edge 52 may be sewn to garment base 12.

Turning now to FIGS. 4-7 and 10, illustrative non-exclusive examples of garments 10 are illustrated. Where appropriate, the reference numerals from the schematic illustrations of FIGS. 2-3, 8-9, and 11-12 are used to designate corresponding parts in FIGS. 4-7 and 10; however, the examples of FIGS. 4-7 and 10 are non-exclusive and do not limit garments 10 to the illustrated examples of FIGS. 4-7 and 10. That is, garments 10 are not limited to the specific examples illustrated in FIGS. 4-7 and 10 and may incorporate any number of the various aspects, configurations, characteristics, properties, etc. of garments 10 that are illustrated in and discussed with reference to the schematic representations of FIGS. 2-3 and/or the examples of FIGS. 4-7 and 10, as well as variations thereof, without requiring the inclusion of all such aspects, configurations, characteristics, properties, etc. For the purpose of brevity, each previously discussed component, part, portion, aspect, region, etc. or variants thereof may not be discussed, illustrated, and/or labeled again with respect to FIGS. 4-7 and 10; however, it is within the scope of the present disclosure that the previously discussed features, variants, etc. may be utilized therewith.

Figure 4:
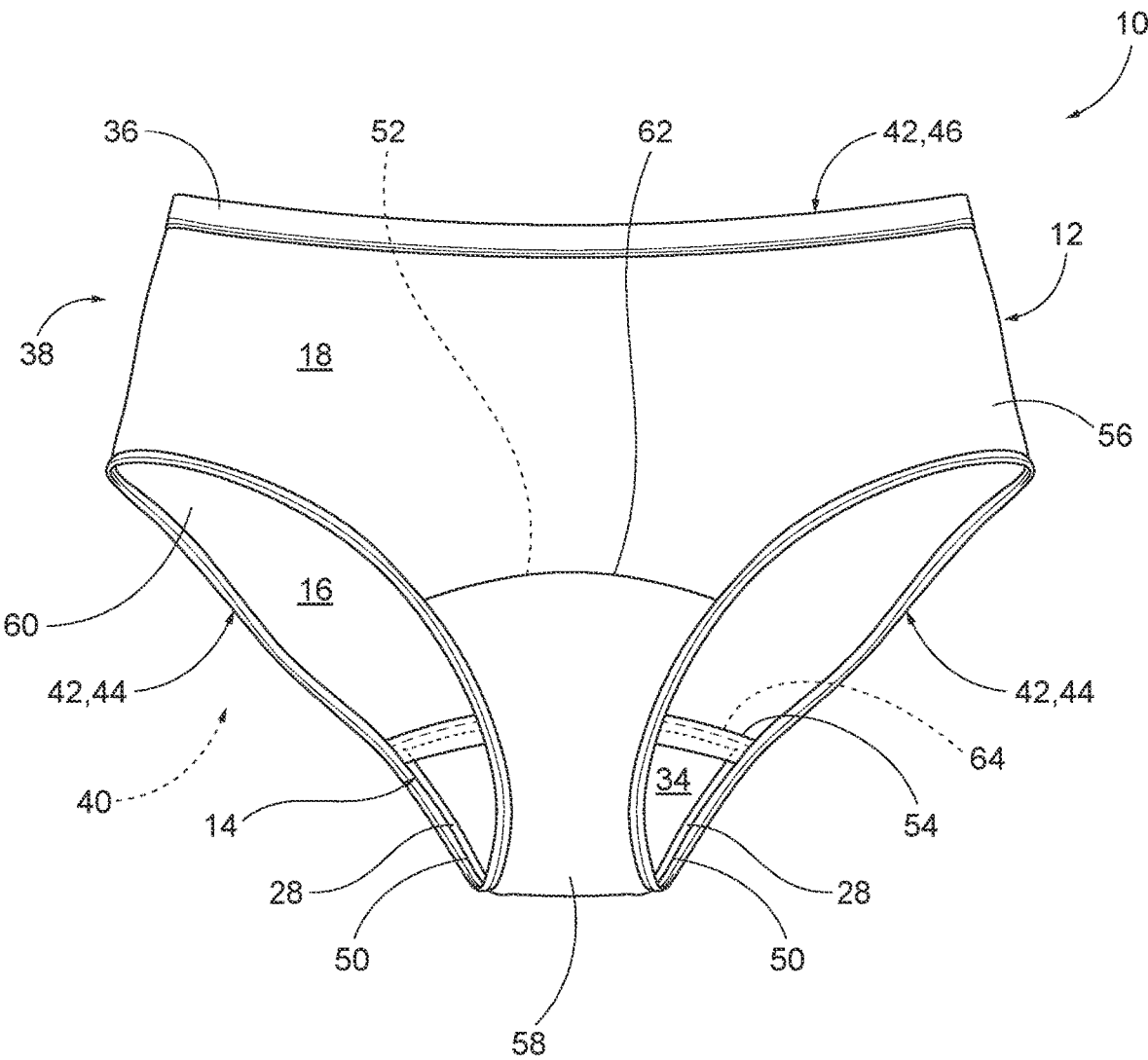
FIG. 4 is a front elevation view of an example of a garment including a fluid retention assembly, according to the present disclosure.

FIG. 4 is a front view of an example of garment 10 viewed from anterior side 38 of garment 10. In some examples, garment 10 is a cut-and-sew garment, with garment base 12 being formed from a plurality of panels. For example, the example of garment 10 shown in FIG. 4 includes a first fabric panel 56, a second fabric panel 58, and a third fabric panel 60, though other examples of garment 10 may be constructed from more or fewer fabric panels. First fabric panel 56 is positioned on anterior side 38 of garment 10, third fabric panel 60 is positioned on posterior side 40 of garment 10, and second fabric panel 58 extends between first fabric panel 56 and third fabric panel 60 in this example. In some examples, the footprint of second fabric panel 58 may be substantially the same as the footprint of fluid retention assembly 14. For example, anterior edge 52 of fluid retention assembly 14 may substantially correspond with an anterior edge 62 of second fabric panel 58, while posterior edge 54 of fluid retention assembly 14 may substantially correspond with a posterior edge 64 of second fabric panel 58. In FIG. 4, fluid retention assembly 14 is partially visible on garment base interior side 16.

Herein, the term "correspond," as used to describe a relative position of a first edge or feature relative to a second edge or feature, generally refers to a configuration in which the first edge or feature and the second edge or feature are positioned at respective locations that are not substantially spatially separated from one another medially, laterally, anteriorly, or posteriorly. However, it is to be understood that a description herein of two or more components as "corresponding" does not necessarily mean that the two or more components are exactly and/or precisely aligned or collinear with one another. For example, as known in the art, garment construction is not perfect, and the imprecision introduced by human- and/or machine-performed manufacturing can introduce slight misalignments between components that nominally are intended or designed to be aligned or collinear with one another. Accordingly, for the purposes of the present disclosure, the term "correspond" is intended to encompass configurations in which the components are perfectly aligned or collinear, as well as configurations in which the components are slightly misaligned as a result of manufacturing tolerances.

Figure 5:
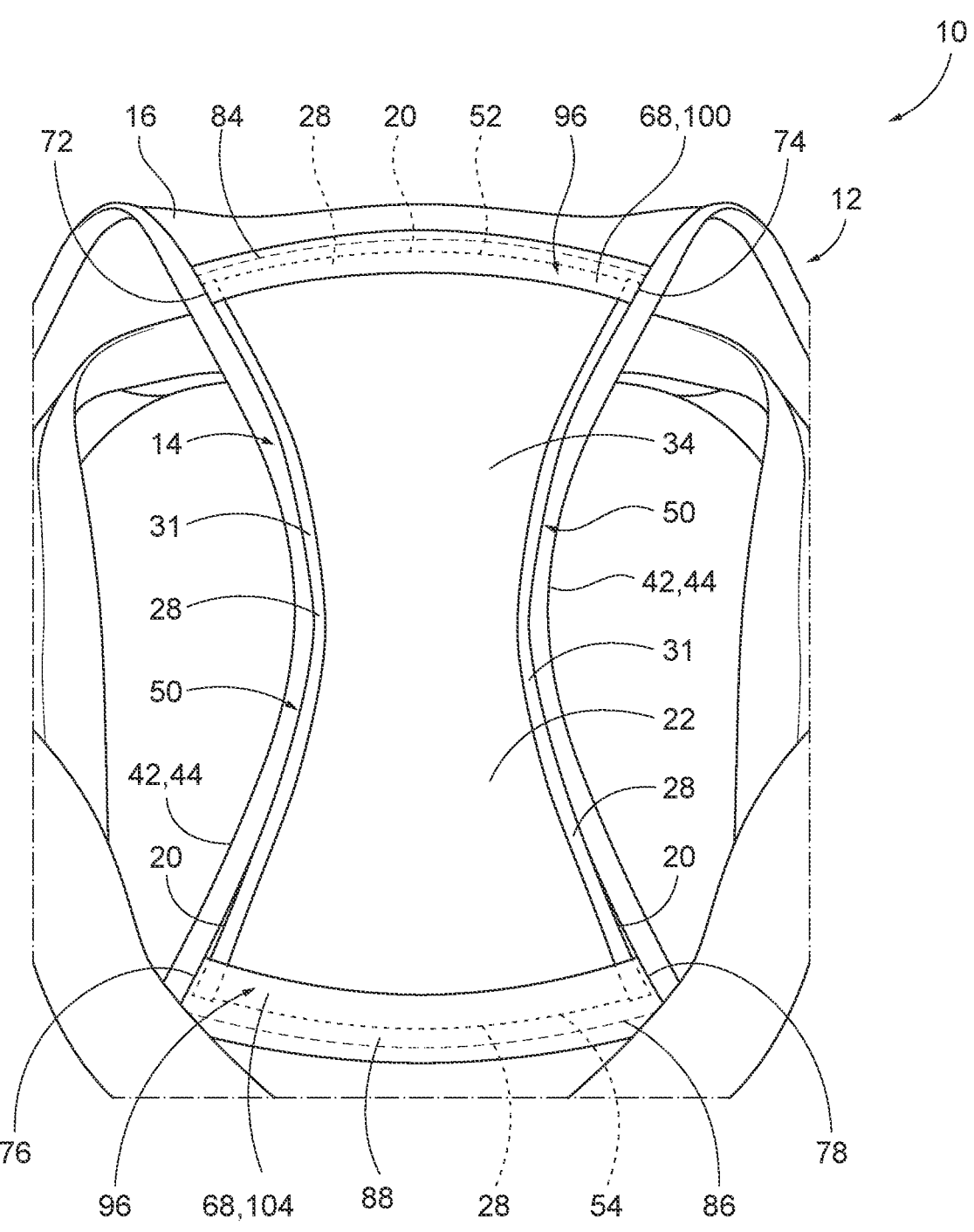
FIG. 5 is a top plan view of an example of a garment including a fluid retention assembly, shown partially inside-out.
Figure 6:
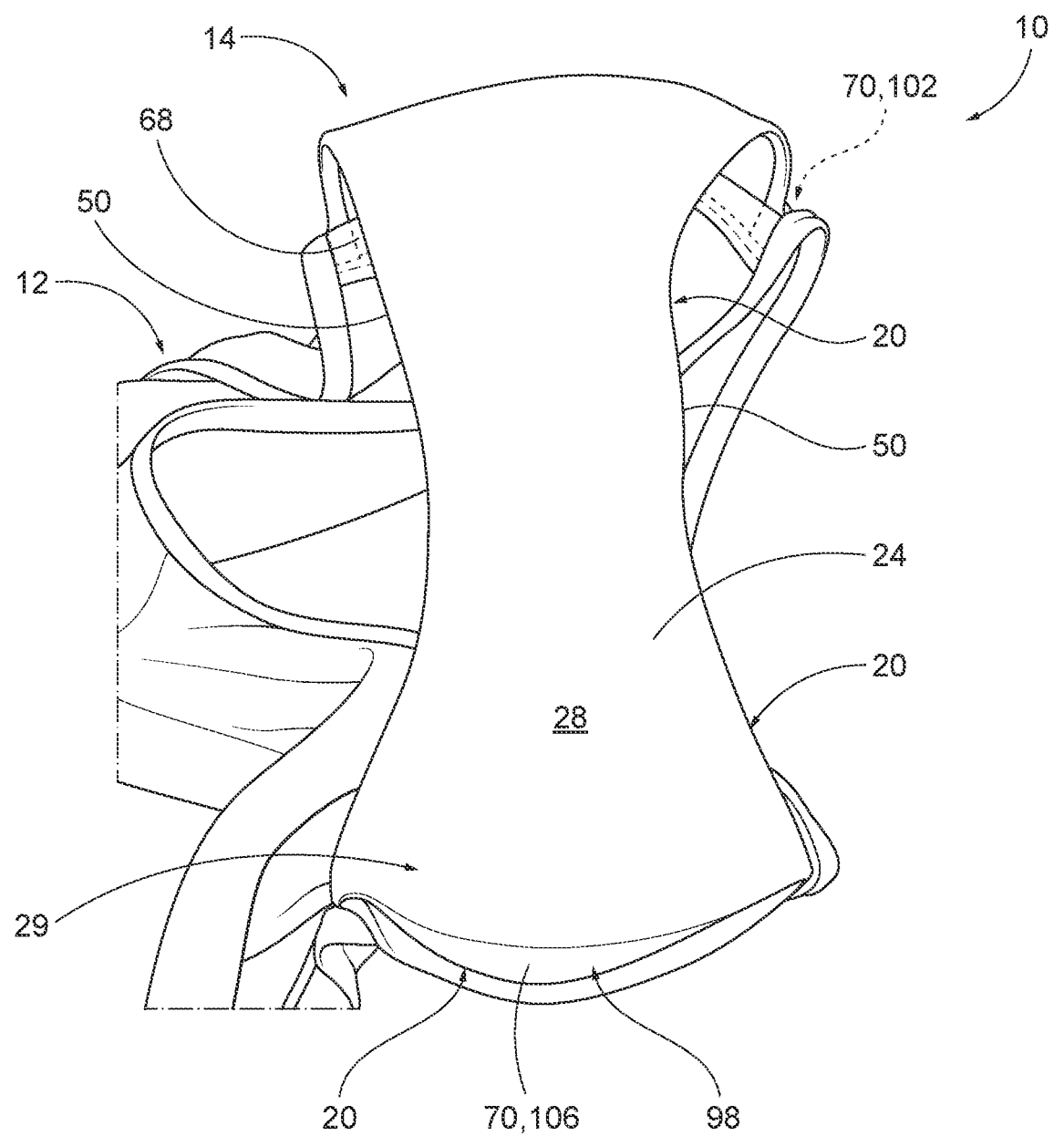
FIG. 6 is a top plan view of the garment of FIG. 5, with the fluid retention assembly flipped inside-out with respect to the garment base.

FIG. 5 shows an example of garment 10 in a partially inside-out state, such that the entire footprint of fluid retention assembly 14 is visible (viewing the assembly interior side 22), while FIG. 6 shows fluid retention assembly 14 flipped with respect to garment base 12, such that assembly exterior side 24 is primarily visible. In some examples, and as shown in FIG. 6, moisture-impermeable layer 28 forms assembly exterior side 24, and wraps around some of outer perimeter 20 of fluid retention assembly 14, namely, moisture-impermeable layer 28 wraps around outer perimeter 20 along at least substantially the entire lengths of opposing lateral edges 50. Though as discussed herein, in other examples of garment 10, moisture-impermeable layer 28 may wrap around substantially all of outer perimeter 20 of fluid retention assembly 14. In yet other examples of garment 10 moisture-impermeable layer 28 may wrap around only a portion of opposing lateral edges 50, along at least substantially all of or a portion of anterior edge 52, and/or along at least substantially all of or a portion of posterior edge 54. Moisture-impermeable layer 28 may extend continuously across assembly exterior side 24, as shown in FIG. 6, to portion or portions 31 that are wrapped around outer perimeter 20.

Figure 7:
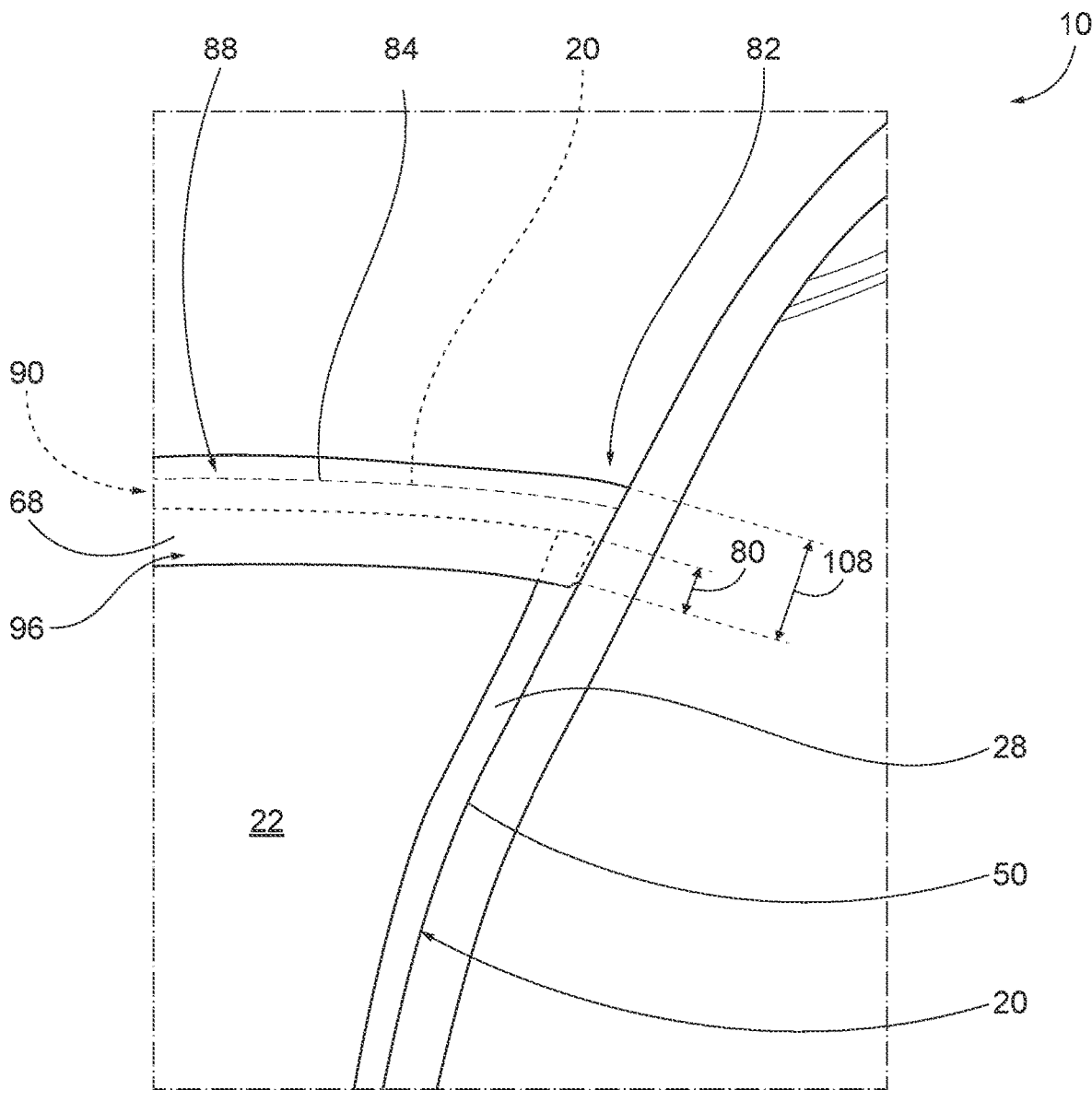
FIG. 7 is a close-up view of one corner of the fluid retention assembly, showing an example of coupling the fluid retention assembly to the garment base.

In some examples, garment 10 may include one or more adhesive bonds 48 along one or more segments, stretches, sections, or portions of outer perimeter 20 of fluid retention assembly 14. For example, anterior edge 52 and/or posterior edge 54 may include a respective adhesive bond 48, which may be configured to seal anterior and/or posterior edges 52, 54 of fluid retention assembly 14. In some examples, each adhesive bond 48 is formed via a first bonding tape 68 and a second bonding tape 70. For example, first bonding tape 68 may be placed on assembly interior side 22, while second bonding tape 70 may be placed on assembly exterior side 24. With reference to FIGS. 5-7, garment 10 may include a respective first bonding tape 68 along some or all of anterior edge 52 of fluid retention assembly 14, a respective second bonding tape 70 along some or all of anterior edge 52 of fluid retention assembly 14, a respective first bonding tape 68 along some or all of posterior edge 54 of fluid retenassembly 14, and/or a respective second bonding tape 70 along some or all of posterior edge 54 of fluid retention assembly 14. Bonding tapes 68, 70 may be, for example, a bonded waterproof tape or a bonded water-resistant tape. Bonding tape 68 may be applied such that at least a portion of bonding tape 68 overlies, or is applied on top of assembly interior side 22 of fluid retention assembly 14. Similarly, bonding tape 70 may be applied such that at least a portion of bonding tape 70 underlies, or is applied against assembly exterior side 24 of fluid retention assembly 14. Bonding tapes 68, 70 may be bonded to each other and to fluid retention assembly 14, but are not bonded to garment base 12 in examples of garment 10.

First bonding tape 68 is primarily visible in FIG. 5, which shows assembly interior side 22 of fluid retention assembly 14, while second bonding tape 70 is primarily visible in FIG. 6, which primarily shows assembly exterior side 24 of fluid retention assembly 14. In the example shown in FIGS. 5-7, anterior edge 52 includes first bonding tape 68 and second bonding tape 70 along the entire length of anterior edge 52, with first bonding tape 68 and second bonding tape 70 extending slightly laterally beyond a first end 72 and a second end 74 of anterior edge 52. First end 72 and second end 74 may also be referred to herein as opposing side edges of anterior edge 52. Similarly, in this example, posterior edge 54 includes first bonding tape 68 and second bonding tape 70 along the entire length of posterior edge 54, with first bonding tape 68 and second bonding tape 70 extending slightly laterally beyond a first end 76 and a second end 78 of posterior edge 54. First end 76 and second end 78 also may be referred to herein as opposing side edges of posterior edge 54.

FIG. 7 shows a close-up view of one corner 82 of the example of fluid retention assembly 14 included in the example of garment 10 shown in FIGS. 5-6, showing an example of placement of bonding tapes 68, 70 with respect to fluid retention assembly 14 and garment base 12. As shown in FIG. 7, moisture-impermeable layer 28 is wrapped around outer perimeter 20 along lateral edge 50 in this example. First bonding tape 68 is visible in FIG. 7, with second portion 96 of bonding tape 68 being bonded to assembly interior side 22 of fluid retention assembly 14 along anterior edge 52. While second portion 96 of bonding tape 68 overlaps and is bonded to assembly interior side 22 of fluid retention assembly 14, first portion 88 of bonding tape 68 extends anteriorly beyond anterior edge 52 of fluid retention assembly 14 such that first portion 88 of bonding tape 68 does not overlap fluid retention assembly 14. As shown in FIG. 7, a small length 80 of lateral edge 50 is covered by second portion 96 of first bonding tape 68 in corner 82 in this example. Additionally, first bonding tape 68 extends a small amount laterally beyond lateral edge 50. The portions of first bonding tape 68 that extend anteriorly beyond anterior edge 52 of fluid retention assembly 14 and laterally beyond lateral edge 50 of fluid retention assembly 14 serve to provide a surface that is bonded or sewn to garment base 12, thereby allowing for indirect coupling of fluid retention assembly 14 to garment base 12 without directly bonding or sewing the fluid retention assembly 14 itself to garment base 12.

While not visible in FIG. 7, second bonding tape 70 underlies fluid retention assembly 14 and first bonding tape 68, such that anterior edge 52 of fluid retention assembly 14 is bonded to and sandwiched between second portion 96 of first bonding tape 68 and second portion 98 of second bonding tape 70. First portion 90 of second bonding tape 70 is bonded to first portion 88 of first bonding tape 68. Seam

84 is visible, in which stitching passes through first portion 88 of first bonding tape 68 and first portion 90 of second bonding tape 70. Seam 84 directly couples bonding tapes 68, 70 to garment base 12, thereby indirectly coupling fluid retention assembly 14 to garment base 12 along anterior edge 52 of fluid retention assembly 14. In this example, seam 84 does not pierce or pass through fluid retention assembly 14, thereby avoiding creating a potential leak point for fluid retention assembly 14. A similar arrangement may be present along posterior edge 54 of fluid retention assembly 14. In other examples of garment 10, however, seam 84 may directly couple fluid retention assembly 14 to garment base 12 and pass through fluid retention assembly along or near anterior edge 52 and/or posterior edge 54, when they are sufficiently spaced away from the primary area of entry of fluids from the wearer's body. In any of the above examples, seam 84 optionally may be stitched using waterproof or water-resistant thread.

Figure 8:
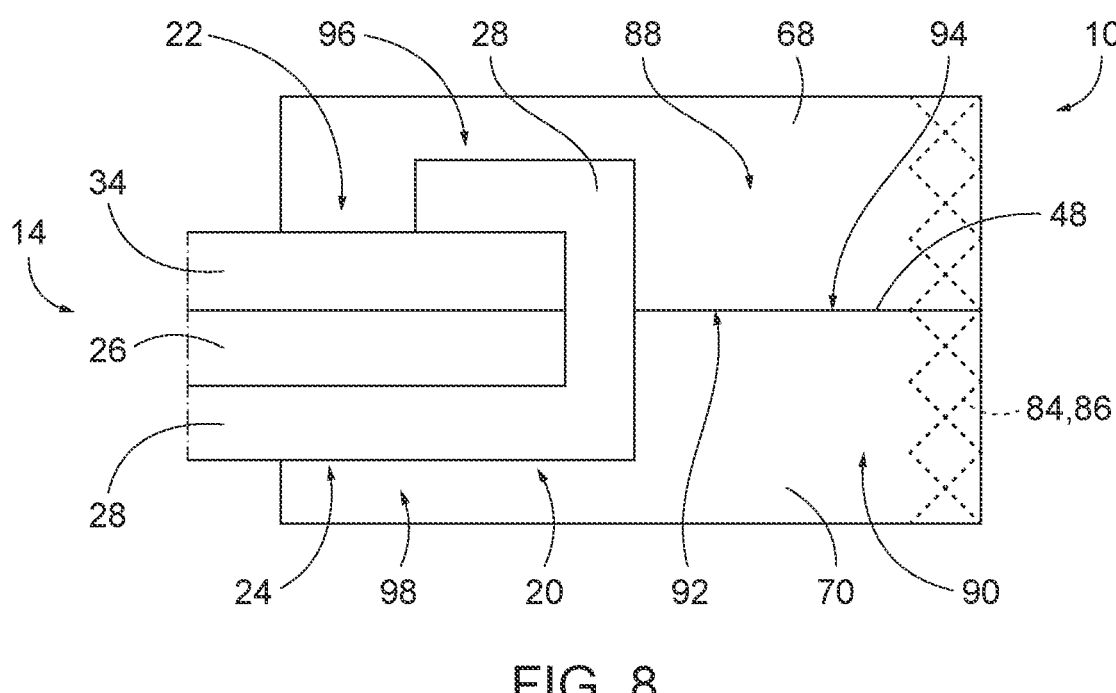
FIG. 8 is a cross-section view of an example of a fluid retention assembly with bonding tapes secured to the outer perimeter.

FIG. 8 shows a schematic cross-sectional view of an example of engagement (e.g., adhesive bond 48) between bonding tapes 68, 70 and fluid retention assembly 14, which may represent a cross-section taken along, for example, line 8-8 in FIG. 3. In the example shown in FIG. 8, moisture-impermeable layer 28 is shown wrapped around the edge of fluid retention assembly 14 along at least a portion of outer perimeter 20, such that moisture-impermeable layer 28 is primarily present on assembly exterior side 24 but also forms a portion of assembly interior side 22 along the portion of outer perimeter 20 that moisture-impermeable layer 28 wraps around absorbent layer 26 and moisture-wicking layer 34. As shown in FIG. 8, in some examples, first and second bonding tapes 68, 70 may be positioned to enclose and/or overlap a portion of outer perimeter 20 where moisture-impermeable layer 28 is folded over onto moisture-wicking layer 34. Such an arrangement may be formed, for example, along some or all of anterior edge 52 and/or along some or all of posterior edge 54 of fluid retention assembly 14.

Figure 9:
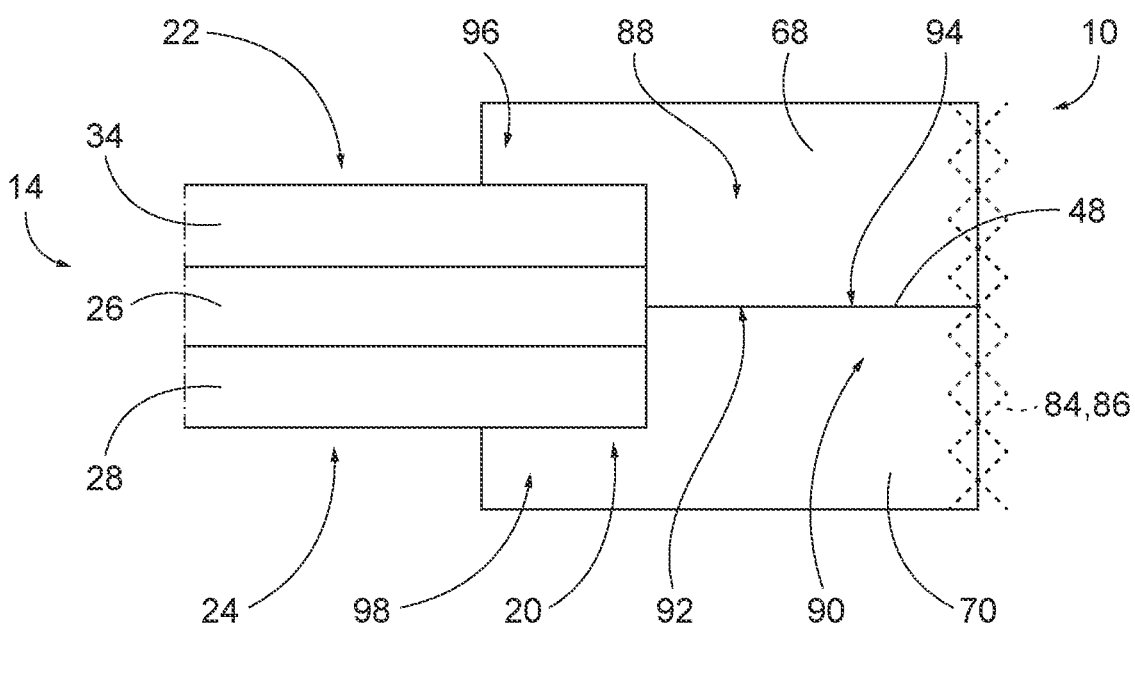
FIG. 9 is a cross-section of another example of a fluid retention assembly with bonding tapes secured to the outer perimeter.

FIG. 9 shows a schematic cross-sectional view of another example of engagement (e.g., adhesive bond 48) between bonding tapes 68, 70 and fluid retention assembly 14, which may represent a cross-section taken along, for example, line 9-9 in FIG. 3. (FIG. 3 schematically represents examples of garment 10 in which portion 31 of moisture-impermeable layer 28 wraps around anterior edge 52 and posterior edge 54 of fluid retention assembly 14, as well as examples of garment 10 in which moisture-impermeable layer 28 does not wrap around anterior edge 52 and posterior edge 54 of fluid retention assembly 14; in either case, one or more bonding tapes 68, 70 may be applied along anterior edge 52 and/or posterior edge 54 in various examples of garment 10). In the example shown in FIG. 9, and in contrast to the example shown in FIG. 8, moisture-impermeable layer 28 does not wrap around absorbent layer 26 and moisture-wicking layer 34 in the area of bonding tapes 68, 70 in this arrangement. As shown in FIG. 9, in some examples, first and second bonding tapes 68, 70 may be positioned to enclose and/or overlap the layers 34, 26, 28 of fluid retention assembly 14 along a portion or all of outer perimeter 20. Such an arrangement may be formed, for example, along some or all of the length of anterior edge 52 and/or along some or all of the length of posterior edge 54 of fluid retention assembly 14.

Figure 10:
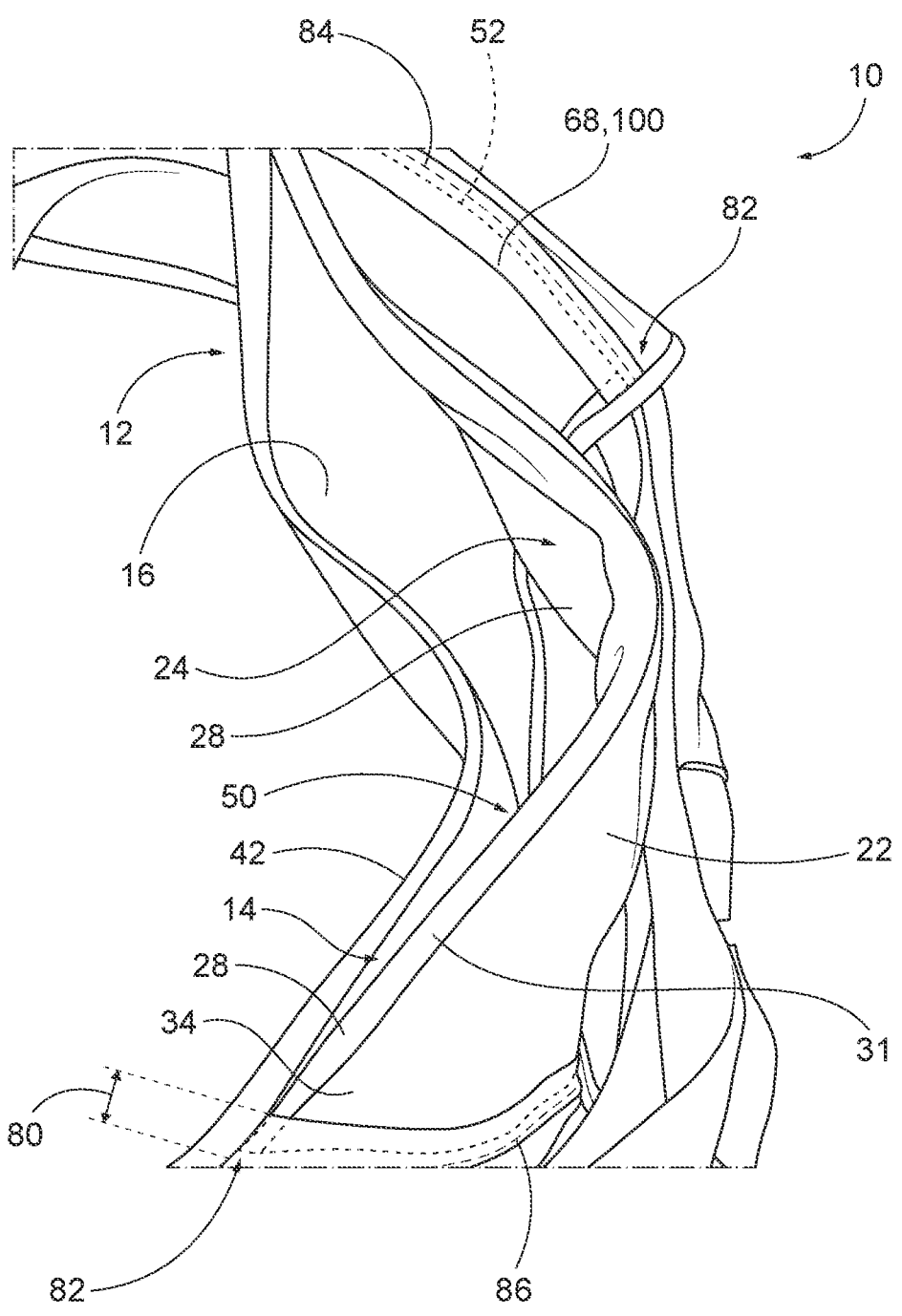
FIG. 10 is a perspective view of an example of a garment showing a relationship between the fluid retention assembly and the garment base.

With primary reference to FIGS. 6, 7, and 10, in some examples, fluid retention assembly 14 is coupled to garment base 12 such that some or all of fluid retention assembly 14 is free to move with respect to garment base 12. For example, in the view shown in FIG. 6, fluid retention assembly 14 is shown flipped inside out (as compared to the view shown in FIG. 5), while being fixed to garment base 12 substantially only along anterior edge 52 and posterior edge 54. As best shown in FIG. 10, opposing lateral edges 50 may be substantially free with respect to garment base 12. In other words, while some or all of the length of anterior edge 52 and posterior edge 54 may be directly or indirectly coupled to garment base 12, a substantial portion of opposing lateral edges 50 of fluid retention assembly 14 are not directly coupled to garment base 12 in some examples. Because of this arrangement, and as shown in FIG. 10, fluid retention assembly 14 may be pulled away from garment base interior side 16, while still remaining secured to garment base 12 along anterior and posterior edges 52, 54. This arrangement also allows for securement of fluid retention assembly 14 to garment base 12 without requiring securement along garment apertures 42, which may facilitate inclusion of disclosed fluid retention assemblies 14 in cut-and-sew garments.

While a substantial majority of opposing lateral edges 50 are free from coupling to garment base 12, in some examples and as shown in FIGS. 7 and 10, a small length 80 of opposing lateral edges 50 may be coupled to garment base 12, such as due to the width of bonding tapes 68, 70 that overlap a small length 80 of opposing lateral edges 50. For example, as indicated in FIGS. 7 and 10, a small length 80 of a respective lateral edge 50 in a respective corner 82 of outer perimeter 20 of fluid retention assembly 14 may be covered by bonding tapes 68, 70, and thereby substantially affixed to garment base 12. In other examples, a small length 80 of lateral edges 50 may be covered by bonding tapes 68, 70 while still being free from being directly coupled to garment base 12. For example, bonding tapes 68, 70 may be bonded to each other while not being bonded to garment base 12 in some examples. In examples of garment 10, at least 75% of the length of lateral edges 50 may be free from being directly coupled to garment base 12, at least 80% of the length of lateral edges 50 may be free from being directly coupled to garment base 12, at least 85% of the length of lateral edges 50 may be free from being directly coupled to garment base 12, at least 90% of the length of lateral edges 50 may be free from being directly coupled to garment base 12, at least 95% of the length of lateral edges 50 may be free from being directly coupled to garment base 12, and/or 100% of the length of lateral edges 50 may be free from being directly coupled to garment base 12.

With continued reference to FIGS. 5 and 7-10, in some examples, fluid retention assembly 14 may be coupled to garment base 12 without any seams directly passing through fluid retention assembly 14 to couple fluid retention assembly 14 to garment base 12. As used herein, fluid retention assembly 14 is said to be coupled without any seams directly coupling it to garment base 12 when seams do not extend through or pierce the fluid retention assembly 14 itself to couple it to garment base 12. For example, seams may be placed through bonding tapes 68, 70 to indirectly couple fluid retention assembly 14 to garment base 12, while avoiding having these seams pierce the layers of fluid retention assembly 14. For example, as shown in FIGS. 5 and 7-10, a first seam 84 may extend along bonding tapes 68, 70 adjacent anterior edge 52 of fluid retention assembly 14, without first seam 84 piercing through fluid retention assembly 14. Similarly, a second seam 86 may extend along bonding tapes 68, 70 adjacent posterior edge 54 of fluid retention assembly 14, without second seam 86 piercing through fluid retention assembly 14. In this manner, seams 84, 86 may effectively indirectly couple fluid retention assembly 14 to garment base 12, while avoiding having the seams 84, 86 pass through moisture-impermeable layer 28, absorbent layer 26, and moisture-wicking layer 34 of fluid retention assembly 14. Instead, seams 84, 86 may directly couple bonding tapes 68, 70 to garment base 12, with bonding tapes 68, 70 in turn being bonded to outer perimeter 20 of fluid retention assembly 14. Additionally or alternatively, anterior edge 52 and posterior edge 54 of outer perimeter 20 of fluid retention assembly 14 may be bonded to garment base 12 via one or more adhesive bonds 48 (e.g., via bonding tapes 68, 70, and/or via other adhesive bonds 48). Seams 84, 86 may be formed using waterproof or water-resistant thread in some examples. As shown in FIGS. 8 and 9, seams 84, 86 may be positioned entirely over the respective bonding tapes 68, 70 (e.g., the entire width of seams 84, 86 may overlap bonding tapes 68 and/or 70), or may be positioned to span an interface between the edge of the respective bonding tapes 68, 70 and garment base 12 (e.g., such that only a portion of the width of seams 84, 86 overlap bonding tapes 68 and/or 70).

Figure 11:
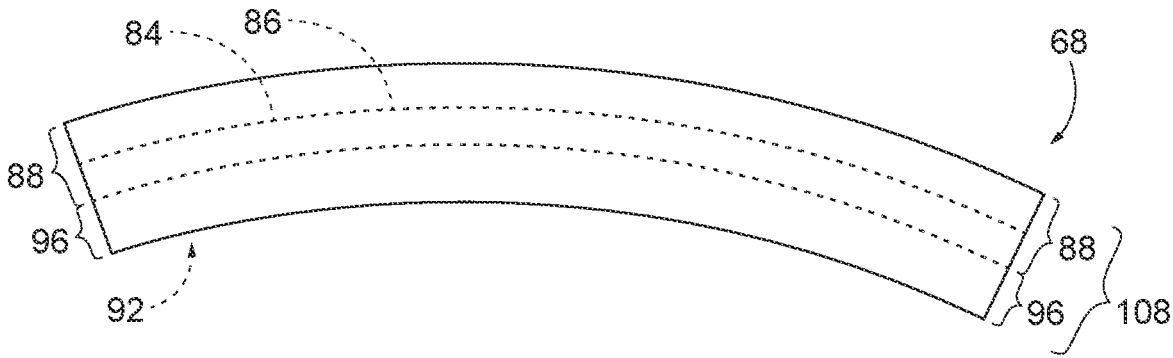
FIG. 11 is a top plan view of an example of an anterior bonding tape that may be secured to fluid retention assemblies of presently disclosed garments.
Figure 12:
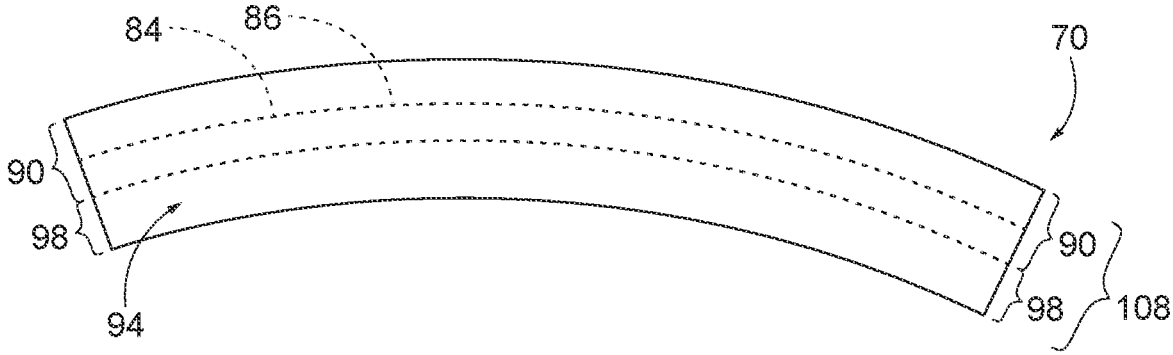
FIG. 12 is a top plan view of an example of a posterior bonding tape that may be secured to fluid retention assemblies of presently disclosed garments.

To accomplish the arrangement described above where bonding tapes 68, 70 are sewn to garment base 12 via seams 84, 86, bonding tapes 68, 70 may be bonded together and also bonded to fluid retention assembly 14. For example, a first portion 88 of first bonding tape 68 may be bonded to a first portion 90 of second bonding tape 70, as best seen in the cross sectional views of FIGS. 8-9. FIGS. 11-12 schematically represent bonding tapes 68, 70, respectively, shown apart from garment 10 for clarity. Specifically, bonding tapes 68, 70 generally have an adhesive side and a non-adhesive side. To bond first portions 88, 90 of bonding tapes 68, 70 together, an adhesive side 92 of the first portion 88 of first bonding tape 68 may be brought to contact with an adhesive side 94 of the first portion 90 of second bonding tape 70, thereby bonding respective first portions 88, 90 of bonding tapes 68, 70 together. In some examples, bonding the bonding tapes 68, 70 may include applying heat and/or pressure to bond first portions 88, 90 together. A respective second portion of each bonding tape 68, 70 may be bonded to fluid retention assembly 14. For example, a second portion 96 of first bonding tape 68 may be bonded to assembly interior side 22 of fluid retention assembly 14, while a second portion 98 of second bonding tape 70 may be bonded to assembly exterior side 24 of fluid retention assembly 14. In practice, one of bonding tapes 68, 70 may be laid down and bonded to fluid retention assembly 14, and then the other of bonding tapes 68, 70 may be bonded to both the fluid retention assembly 14 and the other of the bonding tapes 68, 70 at substantially the same time.

With reference to FIGS. 5, 7-9, and 11-12, first portion 88 of first boding tape 68 and first portion 90 of second bonding tape 70 are sewn to garment base 12 in some examples, such as via seam 84 for bonding tapes 68, 70 adjacent anterior edge 52 of fluid retention assembly 14, or via seam 86 for bonding tapes 68, 70 adjacent posterior edge 54 of fluid retention assembly 14. Bonding tapes 68, 70 may have a width 108. In the schematic representation of FIG. 11, first portion 88 and second portion 96 of first bonding tape 68 are each approximately 50% of the width 108 of first bonding tape 68. In other examples, first and second portions 88, 96 of first bonding tape 68 may have different proportions from one another. For example, first portion 88 of first bonding tape 68 may be at least 25% of width 108, at least 50% of width 108, and/or at least 75% of width 108 in various examples, with second portion 96 making up the remainder. Similarly, in the schematic representation of FIG. 12, first portion 90 and second portion 98 of second bonding tape 70 are each approximately 50% of the width 108 of second bonding tape 70. In other examples, first and second portions 90, 98 of second bonding tape 70 may have different proportions from one another. For example, first portion 90 of second bonding tape 70 may be at least 25% of width 108, at least 50% of width 108, and/or at least 75% of width 108 in various examples, with second portion 98 making up the remainder.

Garment 10 may have respective first bonding tapes 68 along both anterior edge 52 and posterior edge 54 of fluid retention assembly 14, which may be identified respectively as a first anterior bonding tape 100 and a first posterior bonding tape 104 in FIG. 5. Similarly, garment 10 may have respective second bonding tapes 70 along both anterior edge 52 and posterior edge 54 of fluid retention assembly 14, which may be identified respectively as a second anterior bonding tape 102 and a second posterior bonding tape 106 in FIG. 6. Some or all of outer perimeter 20 of fluid retention assembly 14 may be sandwiched between second portions 96, 98 of first and second bonding tapes 68, 70. For example, anterior edge 52 of outer perimeter 20 of fluid retention assembly 14 may be sandwiched between second portion 96 of first anterior bonding tape 100 and second portion 98 of second anterior bonding tape 102. Similarly, posterior edge 54 of outer perimeter 20 of fluid retention assembly 14 may be sandwiched between second portion 96 of first posterior bonding tape 104 and second portion 98 of second posterior bonding tape 106. In some examples of garment 10, bonding tapes 68, 70 are formed using moisture-impermeable materials, optionally of the same material as moisture-impermeable layer 28. In this manner, bonding tapes 68, 70 may be configured to seal, or create a moisture lock around anterior edge 52 and posterior edge 54 (and/or other portions of outer perimeter 20) without moisture-impermeable layer 28 being wrapped around anterior and posterior edges 52, 54 and without bonding fluid retention assembly 14 directly to garment base 12. Though, as discussed herein, various examples of garment 10 are not limited to the same, and it is within the scope of the present disclosure for garments 10 to have a fluid retention assembly 14 bonded to garment base 12, and/or with moisture-impermeable layer 28 wrapped around anterior and/or posterior edges 52, 54 of outer perimeter 20 of fluid retention assembly 14.

In alternative examples of garment 10, anterior edge 52 and/or posterior edge 54 of fluid retention assembly 14 may be directly sewn or stitched to garment base 12, while lateral edges 50 of outer perimeter 20 of fluid retention assembly 14 "float" with respect to garment base 12, as described above. For example, in a given application for garment 10, fluids may be expected to exit the wearer's body in a concentrated region or area of fluid retention assembly 14, though fluid retention assembly 14 may extend over a larger region of garment 10 to provide more absorption as the fluids spread out as they are absorbed by fluid retention assembly 14. In this scenario, while leaks may be problematic in areas of fluid retention assembly 14 nearest to where fluids exit the wearer's body, areas of fluid retention assembly 14 farther away from locations where fluids exit the wearer's body may be less prone to leaks. In a specific illustrative example where garment 10 is configured to absorb menstrual fluids, portions of fluid retention assembly 14 nearest the wearer's pelvic region or crotch area may be free from seams or stitching directly coupling fluid retention assembly 14 to garment base 12 to avoid the potential for side leaks in this area. On the other hand, fluid retention assembly 14 may be large enough such that anterior edge 52 and/or posterior edge 54 may be sufficiently spaced away from the wearer's crotch area such that seams or stitching directly coupling fluid retention assembly 14 to garment base 12 in these areas would not pose a significant risk of leakage.

Within fluid retention assembly 14, moisture-impermeable layer 28 may be directly coupled to moisture-wicking layer 34 only along outer perimeter 20 of fluid retention assembly 14 where moisture-impermeable layer 28 is folded over onto, or wrapped around onto, assembly interior side 22. For example, moisture-impermeable layer 28 may be directly coupled to moisture-wicking layer 34 on assembly interior side 22 along opposing lateral edges 50 of outer perimeter 20 of fluid retention assembly 14. In some examples, moisture-impermeable layer 28 may be folded over onto assembly interior side 22 along anterior edge 52 and/or posterior edge 54 of outer perimeter 20, while in some examples, moisture-impermeable layer 28 is not folded over either anterior edge 52 or posterior edge 54. In other words, in some garments 10, moisture-impermeable layer 28 may be wrapped around outer perimeter 20 onto assembly interior side 22 along at least substantially the entire outer perimeter 20 of fluid retention assembly 14, while in other examples, moisture-impermeable layer 28 is wrapped around outer perimeter 20 along lateral edges 50 of outer perimeter 20, but not wrapped around outer perimeter 20 along anterior edge 52 or posterior edge 54 of outer perimeter 20. In areas of outer perimeter 20 where moisture-impermeable layer 28 is not folded over onto or wrapped around onto assembly interior side 22, moisture-impermeable layer 28 may be substantially co-extensive with one or more other layers of fluid retention assembly 14. For example, as shown in FIG. 9, moisture-impermeable layer 28 may be co-extensive with absorbent layer 26 and moisture-wicking layer 34 in some portions of outer perimeter 20. Additionally or alternatively, moisture-impermeable layer 28, absorbent layer 26, and any moisture-wicking layer 34 are not bonded together or otherwise directly coupled to one another across an expanse of fluid retention assembly 14 in some examples of garment 10.

Figure 13:
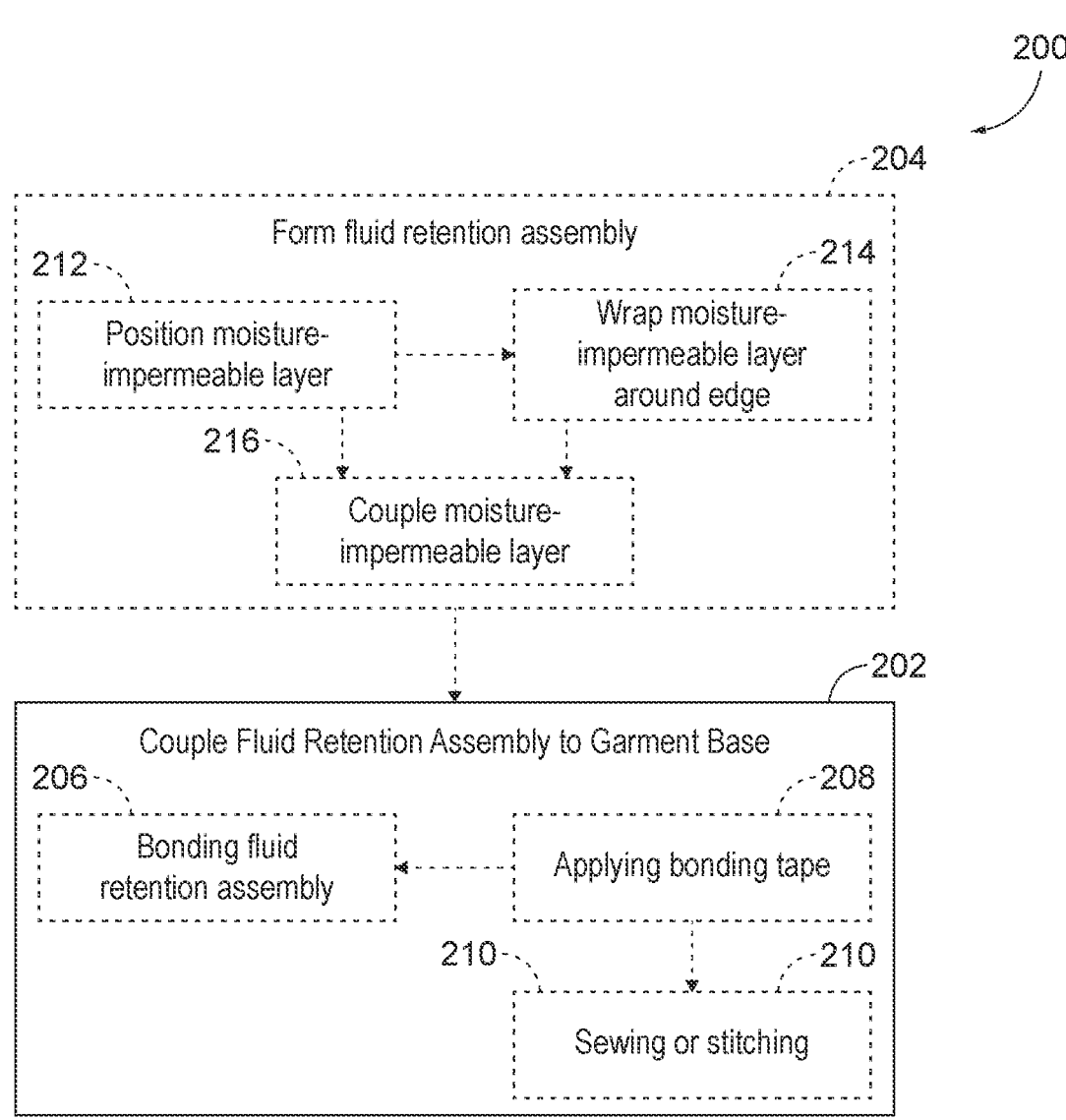
FIG. 13 is a schematic flowchart depicting examples of methods of manufacturing a garment according to the present disclosure.

FIG. 13 schematically provides a flowchart that represents illustrative, non-exclusive examples of methods 200 of manufacturing garments 10 according to the present disclosure. In FIG. 13, some steps are illustrated in dashed boxes indicating that such steps may be optional or may correspond to an optional version of a method according to the present disclosure. That said, not all methods 200 according to the present disclosure are required to include the steps illustrated in solid boxes. The methods 200 and steps illustrated in FIG. 13 are not limiting, and other methods 200 and steps are within the scope of the present disclosure, including methods 200 having greater than or fewer than the number of steps illustrated, as understood from the discussions herein.

Methods 200 include coupling a fluid retention assembly (e.g., fluid retention assembly 14) to an interior side of a garment base (e.g., interior side 16 of garment base 12), at 202. Methods 200 also may include forming the fluid retention assembly at 204 prior to coupling the fluid retention assembly to the garment base at 202. In some methods 200, coupling the fluid retention assembly to the interior side of the garment base at 202 includes bonding the fluid retention assembly to the garment base, at 206, such as bonding an anterior edge (e.g., anterior edge 52) of an outer perimeter (e.g., outer perimeter 20) of the fluid retention assembly to the garment base, and/or bonding a posterior edge (e.g., posterior edge 54) of the outer perimeter of the fluid retention assembly to the garment base. Coupling the fluid retention assembly to the garment base at 202 may include applying one or more bonding tapes, at 208, which may be used to bond the fluid retention assembly to the garment base at 206, or which may be used to seal one or more edges of the fluid retention assembly and then be used to couple the fluid retention assembly to the garment base without bonding it to the garment base. For example, some methods 200 include sewing or stitching at 210 to couple the fluid retention assembly to the garment base. In exemplary methods, a portion of bonding tapes is sewn to the garment base at 210, to couple the fluid retention assembly to the garment base without creating stitching that pierces through the fluid retention assembly, thereby avoiding typical first leak locations in leakproof or leak-resistant garments. Though some methods may include sewing the fluid retention assembly directly to the garment base if desired.

In examples of method 200 including applying bonding tape at 208, the applying bonding tape may include applying one or more anterior bonding tapes (e.g., first anterior bonding tape 100, second anterior bonding tape 102) along some or all of the anterior edge of the outer perimeter of the fluid retention assembly. In some examples, applying the bonding tape at 208 includes applying one or more bonding tapes such that they extend laterally beyond opposing side edges of the anterior edge of the fluid retention assembly. Applying the anterior bonding tape at 208 includes coupling the anterior bonding tape to the anterior edge of the fluid retention assembly and/or to the garment base, such as via bonding the anterior bonding tape or tapes directly to the fluid retention assembly and/or directly to the garment base. Applying the bonding tape at 208 may include applying a first and second anterior bonding tape, such as bonding a portion of the first anterior bonding tape to the assembly interior side along the anterior edge of the fluid retention assembly, and bonding a portion of the second anterior bonding tape to the assembly exterior side along the anterior edge of the fluid retention assembly. The portions of the first and second anterior bonding tapes that are not directly bonded to the fluid retention assembly may be bonded to each other at 208 as well. The portions of the first and second anterior bonding tapes that are bonded together may be sewn or stitched to the garment base at 210, to thereby couple the fluid retention assembly to the garment base without stitching through the fluid retention assembly itself.

Similarly, examples of method 200 that include applying bonding tape at 208 may include applying one or more posterior bonding tapes (e.g., first posterior bonding tape 104, second posterior bonding tape 106) along some or all of the posterior edge of the outer perimeter of the fluid retention assembly. In some examples, applying the bonding tape at 208 includes applying one or more bonding tapes such that they extend laterally beyond opposing side edges of the posterior edge of the fluid retention assembly. Applying the posterior bonding tape at 208 includes coupling the posterior bonding tape to the posterior edge of the fluid retention assembly and/or to the garment base, such as via bonding the posterior bonding tape or tapes directly to the fluid retention assembly and/or directly to the garment base. Applying the bonding tape at 208 may include applying a first and second posterior bonding tape, such as bonding a portion of the first posterior bonding tape to the assembly interior side along the posterior edge of the fluid retention assembly, and bonding a portion of the second posterior bonding tape to the assembly exterior side along the posterior edge of the fluid retention assembly. The portions of the first and second posterior bonding tapes that are not directly bonded to the fluid retention assembly may be bonded to each other at 208 as well. The portions of the first and second posterior bonding tapes that are bonded together may be sewn or stitched to the garment base at 210, to thereby couple the fluid retention assembly to the garment base without stitching through the fluid retention assembly itself.

Disclosed methods 200 may be forming garments via cut-and-sew techniques. Forming the fluid retention assembly at 202 may include positioning the moisture-impermeable layer to underlie the absorbent layer at 212, such that the moisture-impermeable layer separates the garment base interior side from the exterior side of the absorbent layer, wrapping the moisture-impermeable layer around at least a portion of the outer perimeter of the fluid retention assembly at 214, and/or coupling the moisture-impermeable layer to the assembly interior side of the fluid retention assembly at 216, thereby creating a moisture lock around the absorbent layer. Additionally or alternatively, forming the fluid retention assembly at 202 may include sandwiching the absorbent layer between a moisture-wicking layer and the moisture-impermeable layer, with the moisture-wicking layer forming the assembly interior side of the fluid retention assembly.

Illustrative, non-exclusive examples of inventive subject matter according to the present disclosure are described in the following enumerated paragraphs:

A1. A garment configured to be worn by a wearer, the garment comprising:

a garment base comprising a garment base interior side and a garment base exterior side, wherein the garment base interior side faces the wearer when the garment is worn by the wearer, and wherein the garment base exterior side faces outwardly away from the wearer when the garment is worn by the wearer; and a fluid retention assembly coupled to the garment base interior side and having an outer perimeter, wherein the fluid retention assembly comprises:

an assembly interior side that is configured to face the wearer when the garment is worn by the wearer;

an assembly exterior side that is configured to face outwardly away from the wearer when the garment is worn by the wearer, wherein the assembly exterior side faces the garment base interior side;

an absorbent layer configured to absorb fluid excreted from the wearer when the garment is worn, wherein the absorbent layer comprises an absorbent-layer interior side that is configured to face the wearer when the garment is worn by the wearer, and wherein the absorbent layer comprises an absorbent-layer exterior side that is configured to face outwardly away from the wearer when the garment is worn by the wearer; and a moisture-impermeable layer that underlies the absorbent layer and separates the garment base interior side from the absorbent-layer exterior side, wherein the moisture-impermeable layer is configured to restrict fluid from exiting the fluid retention assembly to the garment base interior side, and wherein the moisture-impermeable layer extends to and wraps around at least a portion of the outer perimeter of the fluid retention assembly to form a folded over portion that is coupled to the assembly interior side.

A1.1. The garment of paragraph A1, wherein the moisture-impermeable layer is folded back under itself to form a folded under portion along the portion of the outer perimeter around which the moisture-impermeable layer wraps around.

A1.2. The garment of paragraph A1.1, further comprising a seam with stitches that extend through the folded under portion of the moisture-impermeable layer and the absorbent layer.

A2. The garment of paragraph A1 or A1.1, wherein the moisture-impermeable layer forms the assembly exterior side of the fluid retention assembly.

A2.1. The garment of paragraph A1 or A2, wherein the moisture-impermeable layer is an outermost layer of the fluid retention assembly.

A3. The garment of any of paragraphs A1-A2.1, wherein the moisture-impermeable layer is coupled to the assembly interior side only along the outer perimeter of the fluid retention assembly.

A3.1. The garment of any of paragraphs A1-A3, wherein the moisture-impermeable layer is coupled to the assembly interior side along opposing lateral edges of the outer perimeter of the fluid retention assembly.

A3.2. The garment of any of paragraphs A1-A3.1, wherein the moisture-impermeable layer wraps around opposing lateral edges of the outer perimeter of the fluid retention assembly.

A4. The garment of paragraph A3.1 or A3.2, wherein the opposing lateral edges are adjacent leg openings of the garment.

A5. The garment of any of paragraphs A1-A4, wherein the moisture-impermeable layer creates a moisture lock around the absorbent layer.

A6. The garment of any of paragraphs A1-A5, wherein a substantial length of opposing lateral edges of the outer perimeter of the fluid retention assembly are not bonded or otherwise directly coupled to the garment base.

A7. The garment of any of paragraphs A1-A6, wherein the garment base extends laterally beyond opposing lateral edges of the outer perimeter of the fluid retention assembly.

A8. The garment of paragraph A7, wherein the garment comprises a gap between the fluid retention assembly and leg openings of the garment.

A9. The garment of any of paragraphs A1-A8, wherein no seams directly couple the fluid retention assembly to the garment base.

A10. The garment of any of paragraphs A1-A9, wherein the fluid retention assembly is substantially only directly coupled to the garment base along an anterior edge and a posterior edge of the outer perimeter of the fluid retention assembly.

A10.1. The garment of any of paragraphs A1-A10, wherein the moisture-impermeable layer wraps around an/the anterior edge of the outer perimeter of the fluid retention assembly, and wherein the moisture-impermeable layer wraps around a/the posterior edge of the outer perimeter of the fluid retention assembly.

A11. The garment of any of paragraphs A1-A10.1, wherein an/the anterior edge and a/the posterior edge of the outer perimeter of the fluid retention assembly are bonded to the garment base via one or more adhesive bonds.

A11.1. The garment of any of paragraphs A1-A11, wherein an/the anterior edge and a/the posterior edge of the outer perimeter of the fluid retention assembly each includes one or more adhesive bonds comprising a bonding tape.

A11.2. The garment of paragraph A11.1, wherein the bonding tape comprises a first bonding tape on the assembly interior side of the fluid retention assembly, and wherein the bonding tape comprises a second bonding tape on the assembly exterior side of the fluid retention assembly.

A11.3. The garment of paragraph A11.2, wherein a first portion of the first bonding tape and a first portion of the second bonding tape are bonded together.

A11.4. The garment of paragraph A11.2 or A11.3, wherein a second portion of the first bonding tape is bonded to the assembly interior side of the fluid retention assembly.

A11.5. The garment of any of paragraphs A11.2-A11.4, wherein a second portion of the second bonding tape is bonded to the assembly exterior side of the fluid retention assembly.

A11.6. The garment of any of paragraphs A11.2-A11.5, wherein a/the first portion of the first bonding tape and a/the first portion of the second bonding tape are sewn to the garment base.

A11.7. The garment of any of paragraphs A11.2-A11.6, wherein the first bonding tape comprises a first anterior bonding tape along an/the anterior edge of the outer perimeter of the fluid retention assembly, wherein the first bonding tape comprises a first posterior bonding tape along a/the posterior edge of the outer perimeter of the fluid retention assembly, wherein the second bonding tape comprises a second anterior bonding tape along the anterior edge of the outer perimeter of the fluid retention assembly, and wherein the second bonding tape comprises a second posterior bonding tape along the posterior edge of the outer perimeter of the fluid retention assembly.

A11.8. The garment of paragraph A11.7, wherein the anterior edge of the outer perimeter of the fluid retention assembly is sandwiched between a/the second portion of the first anterior bonding tape and a/the second portion of the second anterior bonding tape.

A11.9. The garment of any of paragraphs A11.7-A11.8, wherein the posterior edge of the outer perimeter of the fluid retention assembly is sandwiched between a/the second portion of the first posterior bonding tape and a/the second portion of the second posterior bonding tape.

A11.10. The garment of any of paragraphs A11.1-A11.9, wherein the bonding tape comprises a first material, and wherein the moisture-impermeable layer also is formed of the first material.

A12. The garment of any of paragraphs A11.1-A11.10, wherein the bonding tape extends laterally beyond opposing side edges of the anterior edge of the outer perimeter of the fluid retention assembly.

A13. The garment of any of paragraphs A11.1-A12, wherein the bonding tape extends laterally beyond opposing side edges of the posterior edge of the outer perimeter of the fluid retention assembly.

A13.1. The garment of any of paragraphs A11.1-A13, wherein the bonding tape is not bonded to the garment base.

A13.2. The garment of any of paragraphs A11.1-A13.1, wherein the bonding tape seals an/the anterior edge of the outer perimeter of the fluid retention assembly and/or a/the posterior edge of the outer perimeter of the fluid retention assembly.

A14. The garment of any of paragraphs A1-A13.2, wherein the fluid retention assembly comprises a mois-ture-wicking layer configured to be positioned against the wearer when the garment is worn.

A15. The garment of paragraph A14, wherein the moisture-wicking layer forms substantially all of the assembly interior side of the fluid retention assembly.

A16. The garment of paragraph A14 or A15, wherein the moisture-impermeable layer, the absorbent layer, and the moisture-wicking layer are not bonded together across an expanse of the fluid retention assembly.

A16.1. The garment of any of paragraphs A14-A16, wherein the moisture-impermeable layer, the absorbent layer, and the moisture-wicking layer are not directly coupled together except along the outer perimeter of the fluid retention assembly.

A16.2. The garment of any of paragraphs A1-A16.1, wherein the moisture-impermeable layer, the absorbent layer, and/or a/the moisture-wicking layer are coupled together via sewing or stitching along and adjacent at least the portion of the outer perimeter of the fluid retention assembly around which the moisture-impermeable layer wraps, and wherein a/the folded over portion of the moisture-impermeable layer is not penetrated by the sewing or stitching.

A16.3. The garment of paragraph A16.2 when depending from paragraph A1.1, wherein the folded under portion of the moisture-impermeable layer is penetrated by the sewing or stitching.

A17. The garment of any of paragraphs A14-A16.3, wherein the absorbent layer is sandwiched between the moisture-wicking layer and the moisture-impermeable layer.

A18. The garment of any of paragraphs A1-A17, wherein the garment is configured to be leakproof.

A19. The garment of any of paragraphs A1-A18, wherein the garment comprises a cut and sew garment.

A20. The garment of any of paragraphs A1-A19, wherein a/the moisture-wicking layer of the fluid retention assembly comprises cotton, carbon cotton, carbon-cotton spandex, and/or a synthetic fiber fabric.

A21. The garment of any of paragraphs A1-A20, wherein a/the moisture-wicking layer of the fluid retention assembly is configured to be quick-drying, odor fighting, and/or anti-microbial.

A22. The garment of any of paragraphs A1-A21, wherein the moisture-impermeable layer is positioned such that it contacts the garment base interior side when the garment is worn.

A23. The garment of any of paragraphs A1-A22, wherein the absorbent layer comprises polyester nylon.

A24. The garment of any of paragraphs A1-A23, wherein the absorbent layer absorbs at least 2 teaspoons (10 ml), at least 3 teaspoons (15 ml), at least 4 teaspoons (20 ml), and/or at least 5 teaspoons (25 ml) of liquid.

A25. The garment of any of paragraphs A1-A24, wherein the moisture-impermeable layer comprises a leak resistant, water resistant, or waterproof fabric or other moisture barrier material, a moisture barrier layer, a moisture barrier film, moisture barrier membrane, a waterproof, water-resistant, or water-repellant treatment, and/or a waterproof, water-resistant, or water-repellant coating.

A26. The garment of any of paragraphs A1-A25, wherein the garment base comprises a four-way stretch fabric that is lightweight, breathable, quick-drying, wicking, and/or odor-resistant.

A27. The garment of any of paragraphs A1-A26, wherein the garment base comprises nylon and elastane.

A28. The garment of any of paragraphs A1-A27, wherein the garment is configured to be machine-washable and re-worn numerous times.

A29. The garment of any of paragraphs A1-A28, wherein the fluid retention assembly has a length that is at least 6 inches (15 cm), at least 7 inches (17.8 cm), at least 8 inches (20 cm), at least 9 inches (22.8 cm), at least 10 inches (25.4 cm), at least 11 inches (28 cm), at least 12 inches (30.5 cm), at least 13 inches (33 cm), at least 14 inches (35.5 cm), and/or at most 15 inches (38 cm) long.

A30. The garment of any of paragraphs A1-A29, wherein the fluid retention assembly is positioned in a region of the garment that is configured to be positioned on, adjacent to, and/or around the wearer's pelvic region when the garment is worn by the wearer.

A31. The garment of any of paragraphs A1-A30, wherein the garment comprises a waistband region; and optionally wherein the garment base at least partially defines the waistband region.

A32. The garment of paragraph A31, wherein the fluid retention assembly does not extend to the waistband region on an anterior side of the garment and/or a posterior side of the garment.

A33. The garment of any of paragraphs A1-A32, wherein the garment defines one or more garment apertures; and optionally wherein the garment base at least partially defines the one or more garment apertures.

A34. The garment of paragraph A33, wherein at least one garment aperture of the one or more garment apertures defines a leg opening that is configured to receive a leg of the wearer when the garment is worn by the wearer.

A35. The garment of any of paragraphs A1-A34, wherein the garment comprises one or more adhesive bonds formed by an adhesive material that is applied to one or both of the garment base and the fluid retention assembly.

A36. The garment of paragraph A35, wherein the adhesive material comprises one or more of a tape, an elastic tape, a film, an elastic film, a spray-on adhesive, and a thermoset adhesive.

A37. The garment of paragraph A35 or A36, wherein the adhesive material is one or more of water-resistant, water-repellent, and waterproof.

A38. The garment of any of paragraphs A1-A37, wherein the garment comprises one or more adhesive bonds formed at least partially via a thermocompression process.

A39. The garment of any of paragraphs A1-A38, wherein the garment base includes one or more base layers.

A40. The garment of any of paragraphs A1-A39, wherein the garment base includes a plurality of base panels that are operatively coupled to one another.

A41. The garment of any of paragraphs A1-A40, wherein the garment base is at least partially formed of one or more of a natural fiber, cotton, a synthetic fiber, polyester, nylon, Spandex™ fabric, and combinations thereof.

A42. The garment of any of paragraphs A1-A41, wherein the garment is an undergarment.

A43. The garment of any of paragraphs A1-A41, wherein the garment is an outerwear garment.

A44. The garment of any of paragraphs A1-A43, wherein the garment is a short (e.g., a pair of shorts).

A45. The garment of any of paragraphs A1-A44, wherein the garment is an activewear garment.

A46. The garment of any of paragraphs A1-A45, wherein one or more of the fluid retention assembly, the absorbent layer, a/the moisture-wicking layer, and the moisture-impermeable layer is at least partially formed of one or more of a natural fiber, cotton, a synthetic fiber, polyester, nylon, Spandex™ fabric, and combinations thereof.

B1. A method of manufacturing the garment of any of paragraphs A1-A46, the method comprising:
coupling the fluid retention assembly to the garment base interior side of the garment base.

B2. The method of paragraph B1, wherein the coupling the fluid retention assembly comprises:
bonding an/the anterior edge of the outer perimeter of the fluid retention assembly to the garment base; and
bonding an/the posterior edge of the outer perimeter of the fluid retention assembly to the garment base.

B3. The method of paragraph B1 or B2, comprising applying an anterior bonding tape along a/the anterior edge of the fluid retention assembly.

B3.1. The method of paragraph B3, wherein the anterior bonding tape extends laterally beyond opposing side edges of the anterior edge of the fluid retention assembly.

B3.2. The method of paragraph B3 or B3.1, wherein the applying the anterior bonding tape comprises coupling the anterior bonding tape to the anterior edge of the fluid retention assembly and to the garment base.

B3.3. The method of any of paragraphs B3-B3.2, wherein the applying the anterior bonding tape comprises bonding the anterior bonding tape to the anterior edge of the fluid retention assembly.

B3.4. The method of any of paragraphs B3-B3.3, wherein the applying the anterior bonding tape comprises applying a first anterior bonding tape and a second anterior bonding tape.

B3.5. The method of paragraph B3.4, wherein the applying the anterior bonding tape comprises:
bonding together a first portion of the first anterior bonding tape and a first portion of the second anterior bonding tape;
bonding a second portion of the first anterior bonding tape to the assembly interior side of the fluid retention assembly; and
bonding a second portion of the second anterior bonding tape to the assembly exterior side of the fluid retention assembly.

B3.6. The method of paragraph B3.5, further comprising sewing or stitching the first portion of the first anterior bonding tape and the first portion of the second anterior bonding tape to the garment base.

B3.7. The method of any of paragraphs B3-B3.3, wherein the applying the anterior bonding tape comprises bonding the anterior bonding tape to the garment base.

B4. The method of any of paragraphs B1-B3.7, comprising applying a posterior bonding tape along a/the posterior edge of the fluid retention assembly.

B4.1. The method of paragraph B4, wherein the posterior bonding tape extends laterally beyond opposing side edges of the posterior edge of the fluid retention assembly.

B4.2. The method of paragraph B4 or B4.1, wherein the applying the posterior bonding tape comprises coupling the posterior bonding tape to the posterior edge of the fluid retention assembly and to the garment base.

B4.3. The method of any of paragraphs B4-B4.2, wherein the applying the posterior bonding tape comprises bonding the posterior bonding tape to the posterior edge of the fluid retention assembly.

B4.4. The method of any of paragraphs B4-B4.3, wherein the applying the posterior bonding tape comprises applying a first posterior bonding tape and a second posterior bonding tape.

B4.5. The method of paragraph B4.4, wherein the applying the posterior bonding tape comprises:

bonding together a first portion of the first posterior bonding tape and a first portion of the second posterior bonding tape;

bonding a second portion of the first posterior bonding tape to the assembly interior side of the fluid retention assembly; and bonding a second portion of the second posterior bonding tape to the assembly exterior side of the fluid retention assembly.

B4.6. The method of paragraph B4.5, further comprising sewing or stitching the first portion of the first posterior bonding tape and the first portion of the second posterior bonding tape to the garment base.

B4.7. The method of any of paragraphs B4-B4.3, wherein the applying the posterior bonding tape comprises bonding the posterior bonding tape to the garment base.

B5. The method of any of paragraphs B1-B4, further comprising forming the garment base via cut-and-sew techniques.

B6. The method of any of paragraphs B1-B5, further comprising, prior to the coupling the fluid retention assembly to the garment base:

forming the fluid retention assembly.

B7. The method of paragraph B6, wherein the forming the fluid retention assembly includes:

positioning the moisture-impermeable layer to underlie the absorbent layer, such that the moisture-impermeable layer separates the garment base interior side from the exterior side of the absorbent layer;

wrapping the moisture-impermeable layer around at least a portion of the outer perimeter of the fluid retention assembly; and coupling the moisture-impermeable layer to the assembly interior side of the fluid retention assembly, thereby creating a moisture lock around the absorbent layer.

B8. The method of any of paragraphs B6-B7, wherein the forming the fluid retention assembly comprises sandwiching the absorbent layer between a/the moisture-wicking layer and the moisture-impermeable layer, wherein the moisture-wicking layer forms the assembly interior side of the fluid retention assembly.

C1. A fluid retention assembly configured to absorb fluid excreted from a wearer, the fluid retention assembly comprising:

an assembly interior side that is configured to face the wearer when the fluid retention assembly is in use;

an assembly exterior side that is configured to face outwardly away from the wearer when the fluid retention assembly is in use;

an absorbent layer configured to absorb fluid excreted from the wearer when the fluid retention assembly is in use, wherein the absorbent layer comprises an absorbent-layer interior side that is configured to face the wearer when the fluid retention assembly is in use, and wherein the absorbent layer comprises an absorbent-layer exterior side that is configured to face outwardly away from the wearer when the fluid retention assembly is in use; and a moisture-impermeable layer that underlies the absorbent layer, wherein the moisture-impermeable layer is configured to restrict fluid from exiting the fluid retention assembly once absorbed by the absorbent layer, and wherein the moisture-impermeable layer extends to and wraps around at least a portion of an outer perimeter of the fluid retention assembly to form a folded over portion that is coupled to the assembly interior side.

C1.1. The fluid retention assembly of paragraph C1, wherein the moisture-impermeable layer is folded back under itself to form a folded under portion along the portion of the outer perimeter around which the moisture-impermeable layer wraps around.

C1.2. The fluid retention assembly of paragraph C1.1, further comprising a seam with stitches that extend through the folded under portion of the moisture-impermeable layer and the absorbent layer.

C2. The fluid retention assembly of any of paragraphs C1-C1.2, wherein the moisture-impermeable layer forms the assembly exterior side of the fluid retention assembly.

C3. The fluid retention assembly of paragraph C1 or C2, wherein the moisture-impermeable layer is an outermost layer of the fluid retention assembly.

C4. The fluid retention assembly of any of paragraphs C1-C3, wherein the moisture-impermeable layer is coupled to the assembly interior side only along the outer perimeter of the fluid retention assembly.

C5. The fluid retention assembly of any of paragraphs C1-C4, wherein the moisture-impermeable layer is coupled to the assembly interior side along opposing lateral edges of the outer perimeter of the fluid retention assembly.

C6. The fluid retention assembly of any of paragraphs C1-C5, wherein the moisture-impermeable layer wraps around opposing lateral edges of the outer perimeter of the fluid retention assembly.

C7. The fluid retention assembly of any of paragraphs C1-C6, wherein the moisture-impermeable layer creates a moisture lock around the absorbent layer.

C8. The fluid retention assembly of any of paragraphs C1-C7, wherein the fluid retention assembly comprises an anterior edge of the outer perimeter and a posterior edge of the outer perimeter, and wherein the fluid retention assembly is configured to be coupled to a garment base substantially only along the anterior edge and the posterior edge.

C9. The fluid retention assembly of any of paragraphs C1-C8, wherein the moisture-impermeable layer wraps around an/the anterior edge of the outer perimeter of the fluid retention assembly, and wherein the moisture-impermeable layer wraps around a/the posterior edge of the outer perimeter of the fluid retention assembly.

C10. The fluid retention assembly of any of paragraphs C1-C9, wherein an/the anterior edge and a/the posterior edge of the outer perimeter of the fluid retention assembly each includes one or more adhesive bonds comprising a bonding tape.

C11. The fluid retention assembly of paragraph C10, wherein the bonding tape comprises a first bonding tape on the assembly interior side of the fluid retention assembly, and wherein the bonding tape comprises a second bonding tape on the assembly exterior side of the fluid retention assembly.

C12. The fluid retention assembly of paragraph C11, wherein a first portion of the first bonding tape and a first portion of the second bonding tape are bonded together.

C13. The fluid retention assembly of paragraph C11 or C12, wherein a second portion of the first bonding tape is bonded to the assembly interior side of the fluid retention assembly.

C14. The fluid retention assembly of any of paragraphs C11-C13, wherein a second portion of the second bonding tape is bonded to the assembly exterior side of the fluid retention assembly.

C15. The fluid retention assembly of any of paragraphs C11-C14, wherein a/the first portion of the first bonding tape and a/the first portion of the second bonding tape are configured to be sewn to a/the garment base.

C16. The fluid retention assembly of any of paragraphs C11-C15, wherein the first bonding tape comprises a first anterior bonding tape along an/the anterior edge of the outer perimeter of the fluid retention assembly, wherein the first bonding tape comprises a first posterior bonding tape along a/the posterior edge of the outer perimeter of the fluid retention assembly, wherein the second bonding tape comprises a second anterior bonding tape along the anterior edge of the outer perimeter of the fluid retention assembly, and wherein the second bonding tape comprises a second posterior bonding tape along the posterior edge of the outer perimeter of the fluid retention assembly.

C17. The fluid retention assembly of paragraph C16, wherein the anterior edge of the outer perimeter of the fluid retention assembly is sandwiched between a/the second portion of the first anterior bonding tape and a/the second portion of the second anterior bonding tape.

C18. The fluid retention assembly of any of paragraphs C16-C17, wherein the posterior edge of the outer perimeter of the fluid retention assembly is sandwiched between a/the second portion of the first posterior bonding tape and a/the second portion of the second posterior bonding tape.

C19. The fluid retention assembly of any of paragraphs C10-C18, wherein the bonding tape comprises a first material, and wherein the moisture-impermeable layer also is formed of the first material.

C20. The fluid retention assembly of any of paragraphs C10-C19, wherein the bonding tape extends laterally beyond opposing side edges of the anterior edge of the outer perimeter of the fluid retention assembly.

C21. The fluid retention assembly of any of paragraphs C10-C20, wherein the bonding tape extends laterally beyond opposing side edges of the posterior edge of the outer perimeter of the fluid retention assembly.

C22. The fluid retention assembly of any of paragraphs C1-C21, wherein the fluid retention assembly comprises a moisture-wicking layer configured to be positioned against the wearer when the fluid retention assembly is in use.

C23. The fluid retention assembly of paragraph C22, wherein the moisture-wicking layer forms substantially all of the assembly interior side of the fluid retention assembly.

C24. The fluid retention assembly of paragraph C22 or C23, wherein the moisture-impermeable layer, the absorbent layer, and the moisture-wicking layer are not bonded together across an expanse of the fluid retention assembly.

C25. The fluid retention assembly of any of paragraphs C22-C24, wherein the moisture-impermeable layer, the absorbent layer, and the moisture-wicking layer are not directly coupled together except along the outer perimeter of the fluid retention assembly.

C26. The fluid retention assembly of any of paragraphs C22-C25, wherein the absorbent layer is sandwiched between the moisture-wicking layer and the moisture-impermeable layer.

C27. The fluid retention assembly of any of paragraphs C1-C26, wherein the fluid retention assembly is configured to be leakproof.

C28. The fluid retention assembly of any of paragraphs C1-C27, wherein a/the moisture-wicking layer of the fluid retention assembly comprises cotton, carbon cotton, carbon-cotton spandex, and/or a synthetic fiber fabric.

C29. The fluid retention assembly of any of paragraphs C1-C28, wherein a/the moisture-wicking layer of the fluid retention assembly is configured to be quick-drying, odor fighting, and/or anti-microbial.

C30. The fluid retention assembly of any of paragraphs C1-C29, wherein the moisture-impermeable layer is positioned such that it is configured to contact a garment base interior side of a garment when the fluid retention assembly is incorporated into the garment.

C31. The fluid retention assembly of any of paragraphs C1-C30, wherein the absorbent layer comprises polyester nylon.

C32. The fluid retention assembly of any of paragraphs C1-C31, wherein the absorbent layer absorbs at least 2 teaspoons (10 ml), at least 3 teaspoons (15 ml), at least 4 teaspoons (20 ml), and/or at least 5 teaspoons (25 ml) of liquid.

C33. The fluid retention assembly of any of paragraphs C1-C32, wherein the moisture-impermeable layer comprises a leak resistant, water resistant, or waterproof fabric or other moisture barrier material, a moisture barrier layer, a moisture barrier film, moisture barrier membrane, a waterproof, water-resistant, or water-repellant treatment, and/or a waterproof, water-resistant, or water-repellant coating.

C34. The fluid retention assembly of any of paragraphs C1-C33, wherein the fluid retention assembly is configured to be machine-washable and re-worn numerous times.

C35. The fluid retention assembly of any of paragraphs C1-C34, wherein the fluid retention assembly has a length that is at least 6 inches (15 cm), at least 7 inches (17.8 cm), at least 8 inches (20 cm), at least 9 inches (22.8 cm), at least 10 inches (25.4 cm), at least 11 inches (28 cm), at least 12 inches (30.5 cm), at least 13 inches (33 cm), at least 14 inches (35.5 cm), and/or at most 15 inches (38 cm) long.

C36. The fluid retention assembly of any of paragraphs C1-C35, wherein the fluid retention assembly is configured to be positioned in a region of a/the garment that is configured to be positioned on, adjacent to, and/or around the wearer's pelvic region when the garment is worn by the wearer.

C37. The fluid retention assembly of any of paragraphs C1-C36, wherein one or more of the fluid retention assembly, the absorbent layer, a/the moisture-wicking layer, and the moisture-impermeable layer is at least partially formed of one or more of a natural fiber, cotton, a synthetic fiber, polyester, nylon, Spandex™ fabric, and combinations thereof.

C38. The fluid retention assembly of any of paragraphs C1-C37, wherein the fluid retention assembly is configured to be incorporated into a/the garment.

C39. The fluid retention assembly of paragraph C38, wherein the fluid retention assembly is configured to be permanently coupled to the garment.

C40. The fluid retention assembly of paragraph C38, wherein the fluid retention assembly is configured to be selectively coupled to and selectively removable from the garment.

C41. The fluid retention assembly of any of paragraphs C38-C40, wherein the fluid retention assembly is configured to be coupled to a/the garment base interior side of the garment, wherein the garment base interior side faces the wearer when the garment is worn by the wearer.

C42. The fluid retention assembly of paragraph C41, wherein the assembly exterior side of the fluid retention assembly faces the garment base interior side when the fluid retention assembly is incorporated into the garment.

C43. The fluid retention assembly of any of paragraphs C41-C42, wherein the moisture-impermeable layer separates the garment base interior side from the absorbent-layer exterior side when the fluid retention assembly is incorporated into the garment.

D1. Use of the garment of any of paragraphs A1-A46 to absorb and retain fluid excretions from the wearer of the garment.

D2. Use of the fluid retention assembly of any of paragraphs C1-C43 to absorb and retain fluid excretions from the wearer of the garment.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, implemented, utilized, programmed, and/or designed for the purpose of performing the function. It is also within the scope of the present disclosure that elements, components, and/or other recited subject matter that is recited as being adapted to perform a particular function may additionally or alternatively be described as being configured to perform that function, and vice versa. Similarly, subject matter that is recited as being configured to perform a particular function may additionally or alternatively be described as being operative to perform that function.

As used herein, the term "and/or" placed between a first entity and a second entity means one of (1) the first entity, (2) the second entity, and (3) the first entity and the second entity. Multiple entries listed with "and/or" should be construed in the same manner, i.e., "one or more" of the entities so conjoined. Other entities optionally may be present other than the entities specifically identified by the "and/or" clause, whether related or unrelated to those entities specifically identified. Thus, as a non-limiting example, a reference to "A and/or B," when used in conjunction with open-ended language such as "comprising," may refer, in one example, to A only (optionally including entities other than B); in another example, to B only (optionally including entities other than A); in yet another example, to both A and B (optionally including other entities). These entities may refer to elements, actions, structures, steps, operations, values, and the like.

As used herein, the phrase "at least one," in reference to a list of one or more entities should be understood to mean at least one entity selected from any one or more of the entities in the list of entities, but not necessarily including at least one of each and every entity specifically listed within the list of entities and not excluding any combinations of entities in the list of entities. This definition also allows that entities may optionally be present other than the entities specifically identified within the list of entities to which the phrase "at least one" refers, whether related or unrelated to those entities specifically identified. Thus, as a non-limiting example, "at least one of A and B" (or, equivalently, "at least one of A or B," or, equivalently "at least one of A and/or B") may refer, in one embodiment, to at least one, optionally including more than one, A, with no B present (and optionally including entities other than B); in another embodiment, to at least one, optionally including more than one, B, with no A present (and optionally including entities other than A); in yet another embodiment, to at least one, optionally including more than one, A, and at least one, optionally including more than one, B (and optionally including other entities). In other words, the phrases "at least one," "one or more," and "and/or" are open-ended expressions that are both conjunctive and disjunctive in operation. For example, each of the expressions "at least one of A, B, and C," "at least one of A, B, or C," "one or more of A, B, and C," "one or more of A, B, or C," and "A, B, and/or C" may mean A alone, B alone, C alone, A and B together, A and C together, B and C together, A, B, and C together, and optionally any of the above in combination with at least one other entity.

As used herein, "substantial," "substantially," the phrase "at least substantially," and the like, when modifying a degree or relationship, includes not only the recited "substantial" degree or relationship, but also the full extent of the recited degree or relationship. A substantial amount of a recited degree or relationship may include at least 75% of the recited degree or relationship. For example, a first component that extends at least substantially around a second component includes a first component that extends around at least 75% of a circumference of the second component and also includes a first component that extends fully circumferentially around the second component.

As used herein, the phrase, "for example," the phrase, "as an example," and/or simply the term "example," when used with reference to one or more components, features, details, structures, embodiments, and/or methods according to the present disclosure, are intended to convey that the described component, feature, detail, structure, embodiment, and/or method is an illustrative, non-exclusive example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure.

The various disclosed elements of apparatuses disclosed herein are not required to all apparatuses according to the present disclosure, and the present disclosure includes all novel and non-obvious combinations and subcombinations of the various elements disclosed herein. Moreover, one or more of the various elements disclosed herein may define independent inventive subject matter that is separate and apart from the whole of a disclosed apparatus. Accordingly, such inventive subject matter is not required to be associated with the specific apparatuses that are expressly disclosed herein, and such inventive subject matter may find utility in apparatuses and/or methods that are not expressly disclosed herein.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. Similarly, when the disclosure or subsequently filed claims recite "a" or "a first" element or the equivalent thereof, such disclosure and/or claims should be understood to include incorporation of one or more such elements, neither requiring nor excluding two or more such elements.

The invention claimed is:

1. A garment configured to be worn by a wearer, the garment comprising:

a garment base comprising a garment base interior side and a garment base exterior side, wherein the garment base interior side faces the wearer when the garment is worn by the wearer, and wherein the garment base exterior side faces outwardly away from the wearer when the garment is worn by the wearer; and a fluid retention assembly coupled to the garment base interior side and having an outer perimeter, wherein a substantial length of opposing lateral edges of the outer perimeter of the fluid retention assembly are not bonded or otherwise directly coupled to the garment base, and wherein the fluid retention assembly comprises:

an assembly interior side that is configured to face the wearer when the garment is worn by the wearer;

an assembly exterior side that is configured to face outwardly away from the wearer when the garment is worn by the wearer, wherein the assembly exterior side faces the garment base interior side;

an absorbent layer configured to absorb fluid excreted from the wearer when the garment is worn, wherein the absorbent layer comprises an absorbent-layer interior side that is configured to face the wearer when the garment is worn by the wearer, and wherein the absorbent layer comprises an absorbent-layer exterior side that is configured to face outwardly away from the wearer when the garment is worn by the wearer; and a moisture-impermeable layer that underlies the absorbent layer and separates the garment base interior side from the absorbent-layer exterior side, wherein the moisture-impermeable layer is configured to restrict fluid from exiting the fluid retention assembly to the garment base interior side, and wherein the moisture-impermeable layer extends continuously across the assembly exterior side and further continues around at least a portion of the outer perimeter of the fluid retention assembly such that the moisture-impermeable layer wraps around at least the portion of the outer perimeter and is coupled to the assembly interior side, wherein an anterior edge of the outer perimeter of the fluid retention assembly and a posterior edge of the outer perimeter of the fluid retention assembly each includes one or more adhesive bonds comprising a bonding tape, wherein the bonding tape comprises a first bonding tape on the assembly interior side of the fluid retention assembly, wherein the bonding tape comprises a second bonding tape on the assembly exterior side of the fluid retention assembly, wherein a first portion of the first bonding tape and a first portion of the second bonding tape are bonded together, wherein a second portion of the first bonding tape is bonded to the assembly interior side of the fluid retention assembly, and wherein a second portion of the second bonding tape is bonded to the assembly exterior side of the fluid retention assembly.

2. The garment according to claim 1, wherein the moisture-impermeable layer forms the assembly exterior side of the fluid retention assembly.

3. The garment according to claim 1, wherein the moisture-impermeable layer is coupled to the assembly interior side only along the outer perimeter of the fluid retention assembly.

4. The garment according to claim 1, wherein the fluid retention assembly is substantially only directly coupled to the garment base along an anterior edge and a posterior edge of the outer perimeter of the fluid retention assembly.

5. The garment according to claim 1, wherein the garment base extends laterally beyond opposing lateral edges of the outer perimeter of the fluid retention assembly, such that the garment comprises a respective gap between each respective lateral edge of the fluid retention assembly and respective leg openings of the garment.

6. The garment according to claim 1, wherein the moisture-impermeable layer wraps around opposing lateral edges of the outer perimeter of the fluid retention assembly.

7. The garment according to claim 6, wherein the moisture-impermeable layer wraps around an anterior edge of the outer perimeter of the fluid retention assembly, and wherein the moisture-impermeable layer wraps around a posterior edge of the outer perimeter of the fluid retention assembly.

8. The garment according to claim 1, wherein the first portion of the first bonding tape and the first portion of the second bonding tape are sewn to the garment base.

9. The garment according to claim 8, wherein the first bonding tape comprises a first anterior bonding tape along the anterior edge of the outer perimeter of the fluid retention assembly, wherein the first bonding tape comprises a first posterior bonding tape along the posterior edge of the outer perimeter of the fluid retention assembly, wherein the second bonding tape comprises a second anterior bonding tape along the anterior edge of the outer perimeter of the fluid retention assembly, and wherein the second bonding tape comprises a second posterior bonding tape along the posterior edge of the outer perimeter of the fluid retention assembly.

10. The garment according to claim 9, wherein the anterior edge of the outer perimeter of the fluid retention assembly is sandwiched between the second portion of the first bonding tape and the second portion of the second bonding tape, and wherein the posterior edge of the outer perimeter of the fluid retention assembly is sandwiched between the second portion of the first bonding tape and the second portion of the second bonding tape.

11. The garment according to claim 1, wherein the fluid retention assembly comprises a moisture-wicking layer configured to be positioned against the wearer when the garment is worn, wherein the moisture-wicking layer forms substantially all of the assembly interior side of the fluid retention assembly, and wherein the absorbent layer is sandwiched between the moisture-wicking layer and the moisture-impermeable layer.

12. The garment according to claim 1, wherein the garment comprises a cut and sew garment, and wherein the garment is configured to be machine-washable and re-worn numerous times.

13. A method of manufacturing a garment configured to be worn by a wearer, wherein the garment comprises:

a garment base comprising a garment base interior side and a garment base exterior side, wherein the garment base interior side faces the wearer when the garment is worn by the wearer, and wherein the garment base exterior side faces outwardly away from the wearer when the garment is worn by the wearer; and a fluid retention assembly coupled to the garment base interior side and having an outer perimeter, wherein a substantial length of opposing lateral edges of the outer perimeter of the fluid retention assembly are not bonded or otherwise directly coupled to the garment base, and wherein the fluid retention assembly comprises:

an assembly interior side that is configured to face the wearer when the garment is worn by the wearer;

an assembly exterior side that is configured to face outwardly away from the wearer when the garment is worn by the wearer, wherein the assembly exterior side faces the garment base interior side;

an absorbent layer configured to absorb fluid excreted from the wearer when the garment is worn, wherein the absorbent layer comprises an absorbent-layer interior side that is configured to face the wearer when the garment is worn by the wearer, and wherein the absorbent layer comprises an absorbent-layer exterior side that is configured to face outwardly away from the wearer when the garment is worn by the wearer; and a moisture-impermeable layer that underlies the absorbent layer and separates the garment base interior side from the absorbent-layer exterior side, wherein the moisture-impermeable layer is configured to restrict fluid from exiting the fluid retention assembly to the garment base interior side, and wherein the moisture-impermeable layer extends continuously across the assembly exterior side and further continues around at least a portion of the outer perimeter of the fluid retention assembly such that the moisture-impermeable layer wraps around at least the portion of the outer perimeter and is coupled to the assembly interior side;

the method comprising:

forming the fluid retention assembly; and coupling the fluid retention assembly to the garment base interior side of the garment base, wherein the coupling the fluid retention assembly comprises:

bonding together a first portion of a first anterior bonding tape and a first portion of a second anterior bonding tape;

bonding a second portion of the first anterior bonding tape to the assembly interior side of the fluid retention assembly along an anterior edge of the fluid retention assembly;

bonding a second portion of the second anterior bonding tape to the assembly exterior side of the fluid retention assembly along the anterior edge of the fluid retention assembly;

bonding together a first portion of a first posterior bonding tape and a first portion of a second posterior bonding tape;

bonding a second portion of the first posterior bonding tape to the assembly interior side of the fluid retention assembly along a posterior edge of the fluid retention assembly; and bonding a second portion of the second posterior bonding tape to the assembly exterior side of the fluid retention assembly along the posterior edge of the fluid retention assembly.

14. The method according to claim 13, further comprising:

sewing or stitching the first portion of the first anterior bonding tape and the first portion of the second anterior bonding tape to the garment base; and sewing or stitching the first portion of the first posterior bonding tape and the first portion of the second posterior bonding tape to the garment base.

15. The method according to claim 13, further comprising forming the garment base via cut-and-sew techniques.

16. The method according to claim 13, wherein the forming the fluid retention assembly comprises:

positioning the moisture-impermeable layer to underlie the absorbent layer, such that the moisture-impermeable layer separates the garment base interior side from the absorbent-layer exterior side;

wrapping the moisture-impermeable layer around at least a portion of the outer perimeter of the fluid retention assembly; and coupling the moisture-impermeable layer to the assembly interior side of the fluid retention assembly, thereby creating a moisture lock around the absorbent layer.

17. The method according to claim 16, wherein the forming the fluid retention assembly further comprises sandwiching the absorbent layer between a moisture-wicking layer and the moisture-impermeable layer, wherein the moisture-wicking layer forms the assembly interior side of the fluid retention assembly.

18. A fluid retention assembly configured to absorb fluid excreted from a wearer, the fluid retention assembly comprising:

an assembly interior side that is configured to face the wearer when the fluid retention assembly is in use;

an assembly exterior side that is configured to face outwardly away from the wearer when the fluid retention assembly is in use;

an absorbent layer configured to absorb fluid excreted from the wearer when the fluid retention assembly is in use, wherein the absorbent layer comprises an absorbent-layer interior side that is configured to face the wearer when the fluid retention assembly is in use, and wherein the absorbent layer comprises an absorbent-layer exterior side that is configured to face outwardly away from the wearer when the fluid retention assembly is in use;

a moisture-impermeable layer that underlies the absorbent layer, wherein the moisture-impermeable layer is configured to restrict fluid from exiting the fluid retention assembly once absorbed by the absorbent layer, wherein the moisture-impermeable layer extends continuously to and wraps around at least a portion of an outer perimeter of the fluid retention assembly to form a folded over portion that is coupled to the assembly interior side, and wherein a folded under portion of the moisture-impermeable layer is folded back under the folded over portion;

a seam with stitches that extend through the folded under portion of the moisture-impermeable layer and the absorbent layer, wherein the stitches do not extend through the folded over portion of the moisture-impermeable layer;

a first bonding tape extending along a first portion of the outer perimeter of the fluid retention assembly, wherein a first portion of the first bonding tape does not overlap the assembly interior side, and wherein a second portion of the first bonding tape overlies and is bonded to the assembly interior side; and a second bonding tape extending along the first portion of the outer perimeter of the fluid retention assembly, wherein a first portion of the second bonding tape does not overlap the assembly exterior side, wherein a second portion of the second bonding tape underlies and is bonded to the assembly exterior side, and wherein the first portion of the first bonding tape is bonded to the first portion of the second bonding tape.

19. A garment configured to be worn by a wearer, the garment comprising:

a garment base comprising a garment base interior side and a garment base exterior side, wherein the garment base interior side faces the wearer when the garment is worn by the wearer, and wherein the garment base exterior side faces outwardly away from the wearer when the garment is worn by the wearer;

a fluid retention assembly coupled to the garment base interior side and having an outer perimeter, wherein the fluid retention assembly comprises:

an assembly interior side that is configured to face the wearer when the garment is worn by the wearer;

an assembly exterior side that is configured to face outwardly away from the wearer when the garment is worn by the wearer, wherein the assembly exterior side faces the garment base interior side;

an absorbent layer configured to absorb fluid excreted from the wearer when the garment is worn, wherein the absorbent layer comprises an absorbent-layer interior side that is configured to face the wearer when the garment is worn by the wearer, and wherein the absorbent layer comprises an absorbent-layer exterior side that is configured to face outwardly away from the wearer when the garment is worn by the wearer;

a moisture-impermeable layer that underlies the absorbent layer and separates the garment base interior side from the absorbent-layer exterior side, wherein the moisture-impermeable layer is configured to restrict fluid from exiting the fluid retention assembly to the garment base interior side, and wherein the moisture-impermeable layer extends continuously to and wraps around at least a portion of the outer perimeter of the fluid retention assembly to form a folded over portion that is coupled to the assembly interior side, and wherein a folded under portion of the moisture-impermeable layer is folded back under the folded over portion; and a seam with stitches that extend through the folded under portion of the moisture- impermeable layer and the absorbent layer, wherein the stitches do not extend through the folded over portion of the moisture-impermeable layer;

a first bonding tape; and a second bonding tape, wherein a first portion of the first bonding tape and a first portion of the second bonding tape are bonded together, wherein a second portion of the first bonding tape is bonded to the assembly interior side of the fluid retention assembly and wherein a second portion of the second bonding tape is bonded to the assembly exterior side of the fluid retention assembly.

20. A garment configured to be worn by a wearer, the garment comprising:

a garment base comprising a garment base interior side and a garment base exterior side, wherein the garment base interior side faces the wearer when the garment is worn by the wearer, and wherein the garment base exterior side faces outwardly away from the wearer when the garment is worn by the wearer;

a fluid retention assembly coupled to the garment base interior side and having an outer perimeter, wherein the fluid retention assembly comprises:

an assembly interior side that is configured to face the wearer when the garment is worn by the wearer;

an assembly exterior side that is configured to face outwardly away from the wearer when the garment is worn by the wearer, wherein the assembly exterior side faces the garment base interior side;

an absorbent layer configured to absorb fluid excreted from the wearer when the garment is worn, wherein the absorbent layer comprises an absorbent-layer interior side that is configured to face the wearer when the garment is worn by the wearer, and wherein the absorbent layer comprises an absorbent-layer exterior side that is configured to face outwardly away from the wearer when the garment is worn by the wearer; and a moisture-impermeable layer that underlies the absorbent layer and separates the garment base interior side from the absorbent-layer exterior side, wherein the moisture-impermeable layer is configured to restrict fluid from exiting the fluid retention assembly to the garment base interior side, and wherein the moisture-impermeable layer extends to and wraps around at least a portion of the outer perimeter of the fluid retention assembly and is coupled to the assembly interior side;

a first bonding tape; and a second bonding tape, wherein a first portion of the first bonding tape and a first portion of the second bonding tape are bonded together, wherein a second portion of the first bonding tape is bonded to the assembly interior side of the fluid retention assembly and wherein a second portion of the second bonding tape is bonded to the assembly exterior side of the fluid retention assembly such that a portion of the outer perimeter of the fluid retention assembly is sandwiched between the second portion of the first bonding tape and the second portion of the second bonding tape, and wherein the first portion of the first bonding tape and the first portion of the second bonding tape are sewn to the garment base.

21. The garment according to claim 1, wherein the moisture-impermeable layer is a single piece that continues along the assembly exterior side of and continues to wrap around at least the portion of the outer perimeter.

22. The garment according to claim 1, wherein the moisture-impermeable layer wraps around an entirety of the outer perimeter of the fluid retention assembly.

23. The garment according to claim 1, wherein the moisture-impermeable layer extends to cover an entirety of the assembly exterior side.

24. The garment according claim 1, wherein the moisture-impermeable layer is coupled to the absorbent layer around at least the portion of the outer perimeter of the fluid retention assembly.

* * * * *